United States Patent
Narain et al.

(10) Patent No.: US 11,001,891 B2
(45) Date of Patent: May 11, 2021

(54) METHODS FOR TREATING PARKINSON'S DISEASE

(71) Applicant: Berg LLC, Framingham, MA (US)

(72) Inventors: Niven Rajin Narain, Cambridge, MA (US); Rangaprasad Sarangarajan, Boylston, MA (US); Vivek K. Vishnudas, Bedford, MA (US); Paula Patricia Narain, Cambridge, MA (US); Jeremy Chaufty, Holliston, MA (US); Stephane Gesta, Arlington, MA (US); Reinhard Roessler, Cambridge, MA (US)

(73) Assignee: Berg LLC, Framingham, MA (US)

( * ) Notice: Subject to any disclaimer, the term of this patent is extended or adjusted under 35 U.S.C. 154(b) by 0 days.

(21) Appl. No.: 15/813,106

(22) Filed: Nov. 14, 2017

(65) Prior Publication Data

US 2018/0135129 A1    May 17, 2018

Related U.S. Application Data

(60) Provisional application No. 62/421,946, filed on Nov. 14, 2016.

(51) Int. Cl.
| | | |
|---|---|---|
| *C12Q 1/6883* | (2018.01) | |
| *C12N 15/113* | (2010.01) | |
| *A61P 25/16* | (2006.01) | |

(52) U.S. Cl.
CPC .......... *C12Q 1/6883* (2013.01); *A61P 25/16* (2018.01); *C12N 15/1137* (2013.01); *C12N 2310/14* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,629,323 B2 | 12/2009 | Surmeier et al. | |
| 8,389,487 B2 | 3/2013 | Bohn et al. | |
| 8,486,626 B2 | 7/2013 | Umansky et al. | |
| 9,014,457 B2 | 4/2015 | Moss et al. | |
| 9,139,580 B2 | 9/2015 | Bourque et al. | |
| 2009/0004112 A1 | 1/2009 | Abeliovich | |
| 2015/0119346 A1 | 4/2015 | Heyman et al. | |
| 2016/0207933 A1 | 7/2016 | Bourque et al. | |

FOREIGN PATENT DOCUMENTS

| | | |
|---|---|---|
| WO | 2006/33446 A2 | 12/2006 |
| WO | 2012/119129 A1 | 9/2012 |
| WO | 2012/177997 A1 | 12/2012 |
| WO | 2013/151577 A1 | 10/2013 |
| WO | 2015/095963 A1 | 7/2015 |
| WO | 2015/157514 A1 | 10/2015 |

OTHER PUBLICATIONS

Mayo clinic Symptoms and causes fo Parkinson's disease; https://www.mayoclinic.org/diseases-conditions/parkinsons-disease/symptoms-causes/syc-20376055, google [online] Mayo Foundation for Medical Education and Research, retrieved on May 30, 2019, pp. 1-4 (Year: 2019).*
Mayo Clinic Diagnosis and treatment of Parkinson's disease; https://www.mayoclinic.org/diseases-conditions/parkinsons-disease/symptoms-causes/syc-20376055, google [online] Mayo Foundation for Medical Education and Reserch, retrieved on May 30, 2019, pp. 1-8 (Year: 2019).*
Xicoy et al. Molecular Neurodegeneration 12:10, pp. 1-11 (Year: 2017).*
Alcalay et al., Glucocerebrosidase activity in Parkinson's disease with and without GBA mutations. Brain. Sep. 2015;138(Pt 9):2648-58.
Betarbet et al., Chronic systemic pesticide exposure reproduces features of Parkinson's disease. Nat Neurosci. Dec. 2000;3(12):1301-6.
Caboni et al., Rotenone, deguelin, their metabolites, and the rat model of Parkinson's disease. Chem Res Toxicol. Nov. 2004;17(11):1540-8.
Chambers et al., Highly efficient neural conversion of human ES and iPS cells by dual inhibition of SMAD signaling. Nat Biotechnol. Mar. 2009;27(3):275-80.
Hawrylycz et al., An anatomically comprehensive atlas of the adult human brain transcriptome. Nature. Sep. 20, 2012;489(7416):391-399.
Jiang et al., Methyl methanesulfonate induces necroptosis in human lung adenoma A549 cells through the PIG-3-reactive oxygen species pathway. Tumour Biol. Mar. 2016;37(3):3785-95.
Kang et al., The critical role of catalase in prooxidant and antioxidant function of p53. Cell Death Differ. Jan. 2013;20(1)117-29.
Kapinya et al., Role of NAD(P)H:quinone oxidoreductase in the progression of neuronal cell death in vitro and following cerebral ischaemia in vivo. J Neurochem. Mar. 2003;84(5):1028-39.
Lee et al., The p53-inducible gene 3 (PIG3) contributes to early cellular response to DNA damage. Oncogene. Mar. 11, 2010;29(10):1431-50.
Park et al., The oncogenic effects of p53-inducible gene 3 (PIG3) in colon cancer cells. Korean J Physiol Pharmacol. Mar. 2017;21(2):267-273.
Porte et al., Three-dimensional structure and enzymatic function of proapoptotic human p53-inducible quinone oxidoreductase PIG3. J Biol Chem. Jun. 19, 2009;284(25)17194-205.
Quan et al., Suppression of p53-inducible gene 3 is significant for glioblastoma progression and predicts poor patient prognosis. Tumour Biol. Mar. 2017;39(3):1010428317694572. 9 pages.
Richards et al., Discovery and characterization of an inhibitor of glucosylceramide synthase. J Med Chem. May 10, 2012;55(9):4322-35.

(Continued)

*Primary Examiner* — Brian Whiteman
(74) *Attorney, Agent, or Firm* — McCarter & English, LLP; Jill Mello

(57) ABSTRACT

The present invention provides methods for treating Parkinson's Disease (PD), e.g., PD associated with a genetic mutation in a glucocerebrosidase (GBA) gene or a leucine rich repeat kinase 2 (LRRK2) gene. The methods comprise administering to the subject a modulator, e.g., an inhibitor, of p53-inducible gene 3 (PIG3).

16 Claims, 20 Drawing Sheets

Specification includes a Sequence Listing.

(56) References Cited

OTHER PUBLICATIONS

Shi et al., Human cerebral cortex development from pluripotent stem cells to functional excitatory synapses. Nat Neurosci. Feb. 5, 2012;15(3):477-86.
Shihabuddin et al., Inhibition of glucosylceramide synthase reduces pathology and improves cognition in synucleinopathy murine models. Movement Disorders. 31(Suppl. 2):Abstract 1921, 1 page, Jun. 23, 2016.
Thaler et al., The LRRK2 G2019S mutation as the cause of Parkinson's disease in Ashkenazi Jews. J Neural Transm (Vienna). Nov. 2009;116(11):1473-82.
Vousden et al., p53 and metabolism. Nat Rev Cancer. Oct. 2009;9(10):691-700.
Chen et al., (G2019S) LRRK2 activates MKK4-JNK pathway and causes degeneration of SN dopaminergic neurons in a transgenic mouse model of PD. Cell Death Differ. Oct. 2012;19(10):1623-33.
Iaccarino et al., Apoptotic mechanisms in mutant LRRK2-mediated cell death. Hum Mol Genet. Jun. 1, 2007;16(11)1319-26.
Li et al., Novel LRRK2 GTP-binding inhibitors reduced degeneration in Parkinson's disease cell and mouse models. Hum Mol Genet. Dec. 1, 2014;23(23):6212-22.
Davidson et al., Current prospects for RNA interference-based therapies. Nat Rev Genet. 2011;12(5):329-340.
Nayak et al., p53-Induced apoptosis and inhibitors of p53. Curr Med Chem. 2009;16(21):2627-2640.

\* cited by examiner

METHODS FOR TREATING PARKINSON'S DISEASE

RELATED APPLICATIONS

This application claims priority to U.S. Provisional Application No. 62/421,946, filed on Nov. 14, 2016, the entire contents of which are hereby incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 14, 2017, is named 2017_11_14_19992_18302_ST25.txt and is 34,154 bytes in size.

BACKGROUND OF THE INVENTION

Parkinson's Disease (PD) is the second most common neurodegenerative disorder after Alzheimer's disease affecting approximately 1-2% of the population over 60 years and 4% above 85 years. It is clinically characterized by rigidity, bradykinesia, tremor, postural instability, as well as other clinical features, such as dementia and depression. Pathologically it is identified by a selective degeneration of dopaminergic neurons in the substantia nigra in the midbrain and eventually the presence of Lewy bodies, or abnormal protein aggregates, in the surviving neurons. The etiology of PD is multifactorial and involves complex interactions between genetic and environmental factors, although the exact molecular mechanism underlying the pathogenesis of the disease remains obscure.

In at least some cases, development of PD is genetically driven. In the past 17 years, genetic studies of PD families consolidate the hypothesis that PD has a significant genetic component. Indeed, 14 genes have been described for Mendelian PD so far. For example, familial cases of Parkinson disease can be caused by mutations in the LRRK2, PARK7, PINK1, PRKN, or SNCA genes. Mutations in some of these genes may also play a role in cases that appear to be sporadic (i.e., not inherited). Alterations in certain genes, including GBA and UCHL1, do not cause Parkinson disease but appear to modify the risk of developing the condition in some families.

Mutations in the LRRK2 gene are the most frequently reported monogenic cause of PD and are common in both early and late-onset PD, occurring in both familial and sporadic PD patients with a wide variety of clinical and pathological features and a variable frequency depending on ethnic origin. Among these mutations, the glycine to serine substitution G2019S, located within the protein kinase domain encoded by exon 41, is the most common and was estimated by the international LRRK2 consortium to represent 1% of sporadic and 4% of familial PD patients worldwide. Clinically, the G2019S mutation carriers develop a very similar PD disease to noncarriers, including the development of motor symptoms and cognitive impairment, but some differences could be observed even within the same family Mutations in the glucocerebrosidase gene (GBA) are also associated with PD. Homozygous or compound heterozygous mutations in GBA were initially discovered in patients suffering from Gaucher Disease (GD), a lysosomal-storage disease. Single heterozygous mutations in GBA were initially thought to be non-pathogenic, but, following investigation of early reports of Parkinsonism in GD patients and their heterozygote carrier family members unaffected by GD, it was found that heterozygote mutations confer a significant risk for developing PD. Heterozygotes have a 10-30% chance of developing PD by age 80, which constitutes a 20-fold increase compared to non-carriers, and approximately 5-25% of "idiopathic" PD patients carry GBA mutations, making GBA mutations the greatest risk factor for PD discovered to date.

Presently, knowledge about the patient's mutation status does not alter therapeutic management, since targeted, neuroprotective therapies are still at an experimental stage. Current treatment for PD involves the use of various medications to help control the symptoms and manage problems associated with walking, movement and tremor.

Nevertheless, more effective therapies capable of better managing, slowing down or stopping the progression of PD, e.g., PD associated with a mutation in the GBA gene or an LRRK2 gene, are needed.

SUMMARY OF THE INVENTION

Accordingly, the present invention provides novel methods for treating Parkinson's Disease (PD). In some embodiments, the PD is idiopathic PD, i.e., PD of unknown cause. In some embodiment, the PD is associated with a genetic mutation, e.g., a mutation in glucocerebrosidase gene (GBA) gene or leucine rich repeat kinase 2 (LRRK2). The present invention is based on a surprising discovery of the involvement of PIG3 in the development of PD pathology. Specifically, it was discovered that the p53-inducible protein 3 (PIG3), encoded by the TP53I3 gene, modulates the pathologic development of PD in cells derived from idiopathic PD subjects and from subjects with an LRRK2 mutation. An association between PIG3 and GCase activity was also discovered in LRRK2 mutant cells. Thus, PIG3 represents a novel target for a PD therapy. Accordingly, the methods for treating PD provided by the present invention comprise administering to a subject in need thereof a modulator of p53-inducible gene 3 (PIG3), e.g., an inhibitor of PIG3.

In one aspect, the present invention provides methods of treating PD in a subject in need thereof. In some embodiments, the present invention provides methods of treating PD in a subject in need thereof, wherein the PD is associated with a genetic mutation in a gene selected from the group consisting of glucocerebrosidase (GBA) and leucine rich repeat kinase 2 (LRRK2). In other embodiments, the present invention provides methods for treating idiopathic PD. The methods comprise administering to the subject a modulator, e.g., inhibitor, of PIG3, thereby treating the PD in the subject.

In one aspect, the present invention provides a method of treating Parkinson's disease in a subject in need thereof, wherein the Parkinson's Disease (PD) is associated with a genetic mutation in the leucine rich repeat kinase 2 (LRRK2) gene, comprising identifying the subject as having a genetic mutation in the LRRK2 gene; and administering to the subject a modulator of p53-inducible gene 3 (PIG3) (PIG3 modulator) (e.g., a PIG3 inhibitor), thereby treating the Parkinson's disease in the subject.

In another aspect, the present invention provides a method of treating Parkinson's disease in a subject in need thereof, wherein the Parkinson's Disease (PD) is associated with a genetic mutation in the glucocerebrosidase (GBA) gene, comprising identifying the subject as having a genetic mutation in the GBA gene; and administering to the subject a modulator of p53-inducible gene 3 (PIG3) (PIG3 modulator) (e.g., a PIG3 inhibitor), thereby treating the Parkinson's disease in the subject.

In another aspect, the present invention provides a method of reducing or preventing neuronal cell death in a subject afflicted with PD that comprises administering to the subject a PIG3 modulator, e.g., inhibitor, thereby reducing or preventing neuronal cell death in the subject. In a specific embodiment, the cell death is leucine rich repeat kinase 2 (LRRK2)-mediated neuronal cell death in the subject afflicted with Parkinson's Disease (PD), and wherein the Parkinson's disease is associated with a genetic mutation in the LRRK2 gene. In another specific aspect, the neuronal cell death is glucocerebrosidase-mediated neuronal cell death in the subject afflicted with Parkinson's Disease (PD), and wherein the Parkinson's disease is associated with a genetic mutation in the GBA gene.

In still other aspects, the present invention provides a method of reducing or preventing leucine rich repeat kinase 2 (LRRK2)-mediated neuronal cell death in a subject afflicted with PD, wherein the PD is associated with a genetic mutation in the LRRK2 gene, comprising identifying the subject as having a genetic mutation in the LRRK2 gene; and administering to the subject a PIG3 modulator, e.g., inhibitor. In another aspect, the present invention provides a method of reducing or preventing glucocerebrosidase-mediated neuronal cell death in a subject afflicted with PD, wherein the PD is associated with a genetic mutation in the GBA gene, comprising identifying the subject as having a genetic mutation in the GBA gene; and administering to the subject a PIG3 modulator, e.g., inhibitor.

In yet another aspect, the present invention provides a method of treating Parkinson's Disease (PD) in a subject in need thereof, wherein the Parkinson's Disease is associated with a genetic mutation in the glucocerebrosidase (GBA) gene. The method comprises administering to the subject a modulator of p53-inducible gene 3 (PIG3) (PIG3 modulator) (e.g., a PIG3 inhbitor) in combination with a modulator of glucosylceramide synthase (GCS modulator) (e.g., a GCS inhibitor), thereby treating the Parkinson's disease in the subject. In a specific embodiment, the GCS modulator (e.g., inhibitor) is selected from the group consisting of GZ/SAR402671 and GZ667161.

In various embodiments of the foregoing aspects, the genetic mutation in the LRRK2 gene is selected from the group consisting of G2019S mutation, R1441C mutation, R1441G mutation, R1441H mutation, Y1699C mutation, I2020T mutation and N1437H mutation. In a specific embodiment, the genetic mutation in the LRRK2 gene is the G2019S mutation.

In some embodiments of the foregoing aspects, the genetic mutation in the GBA gene is selected from the group consisting of N370S and L444P.

In some embodiments of the foregoing aspects, at least one symptom of PD is alleviated in the subject, e.g., a symptom of PD is selected from the group consisting of tremor, bradykinesia, muscle rigidity, reduction in speech and swallowing problems.

In some embodiments of the foregoing aspects, administering the PIG3 modulator to the subject results in inhibition or in slowing down the PD progression in the subject, e.g., as measured by UPDRS.

In some aspects of the foregoing aspects, the modulator of PIG3 is an inhibitor of PIG3. In some embodiments, the PIG3 modulator, e.g., inhibitor, is a small molecule or a nucleic acid. In a further embodiment, the nucleic acid comprises an antisense nucleic acid molecule, a double stranded nucleic acid molecule, or an RNA molecule selected from the group consisting of an siRNA, an miRNA, an shRNA, and a dicer substrate siRNA (DsiRNA). In some embodiments, the PIG3 modulator, e.g., inhibitor, is a peptide. In other embodiments, the PIG3 modulator, e.g., inhibitor, is an antibody or antigen-binding fragment thereof.

BRIEF DESCRIPTION OF THE DRAWINGS

FIG. 7, Panel B is a bar graph showing the relative amount of SH-SY5Y cell death as a function of rotenone concentration.

FIG. 8, Panel B is a bar graph showing the relative amount of SH-SY5Y cell death as a function of 6-OHDA concentration.

FIG. 10, Panel B is a bar graph showing the relative amount of cell death in SH-SY5Y cells treated with different concentrations of 6-OHDA in the presence of PIG3 siRNA or NTC.

FIG. 11, Panel B is a bar graph showing the relative amount of cell death in SH-SY5Y cells treated with rotenone and 6-OHDA in the absence and presence of SB23580. FIG. 11, Panel C is a bar graph showing the relative expression of PIG3 mRNA in SH-SY5Y cells treated with rotenone and 6-OHDA in the absence and presence of SB23580.

FIG. 12, Panel B is a bar graph showing the relative amount of cell death in SH-SY5Y cells treated with rotenone and 6-OHDA in the absence and presence of LRRK2-IN-1.

FIG. 14, Panel B is a bar graph showing relative amount of basal ROS in SH-SY5Y cells overexpressing PIG ORF as compared to control.

FIG. 16, Panel B is a bar graph showing the relative amount of PIG3 mRNA as a function of rotenone concentration.

FIG. 17, Panel B is a bar graph showing the relative amount of PIG3 mRNA as a function of 6-OHDA concentration.

FIG. 18, Panel B is a bar graph showing the amount of MKK3 phosphorylation in LRRK2-PD fibroblasts and controls. FIG. 18, Panel C is a bar graph showing the total amount of p53 in the LRRK2-PD fibroblasts and controls. FIG. 18, Panel D is a bar graph showing the total amount of p53 phosphorylation in the LRRK2-PD fibroblasts and controls. FIG. 18, Panel E is a boxplot showing the relative amounts of PIG3 protein in iPSC-derived neurons prepared from the LRRK2-PD fibroblasts and controls. FIG. 18, Panel F is a boxplot showing the relative amounts of p53 protein in the iPSC-derived neurons prepared from the LRRK2-PD fibroblasts and controls.

FIG. 19, Panel B is a bar graph showing the amount of cleaved PARP protein in LRRK2-PD neurons and controls as a function of increasing concentrations of rotenone.

FIG. 20, Panel B is a bar graph showing the amount of cleaved PARP protein LRRK2-PD neurons and controls as a function of increasing concentrations of 6-OHDA.

DETAILED DESCRIPTION OF THE INVENTION

Figure 1:
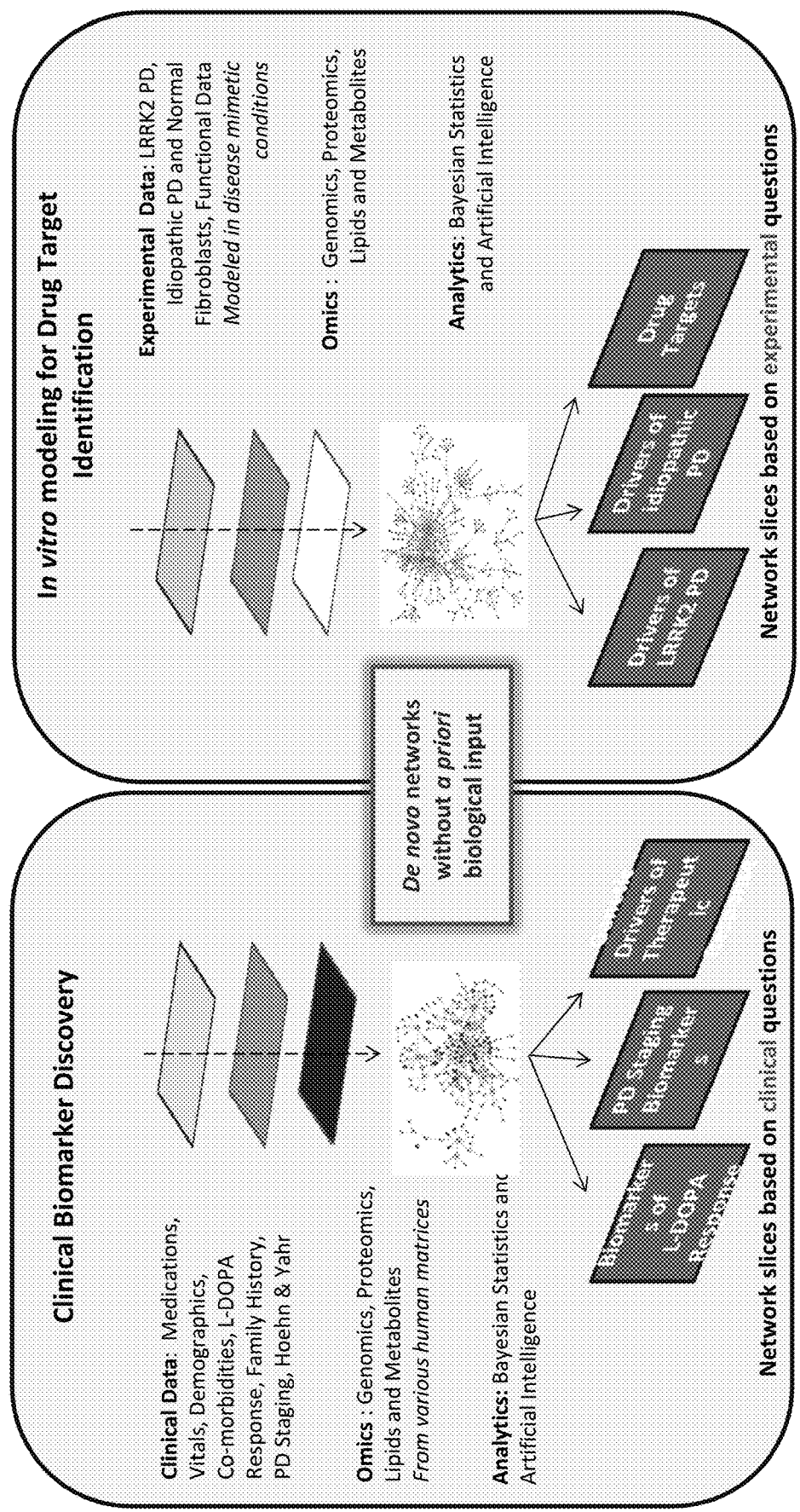
FIG. 1 is a schematic illustration of the Interrogative Biology® Platform.
Figure 2:
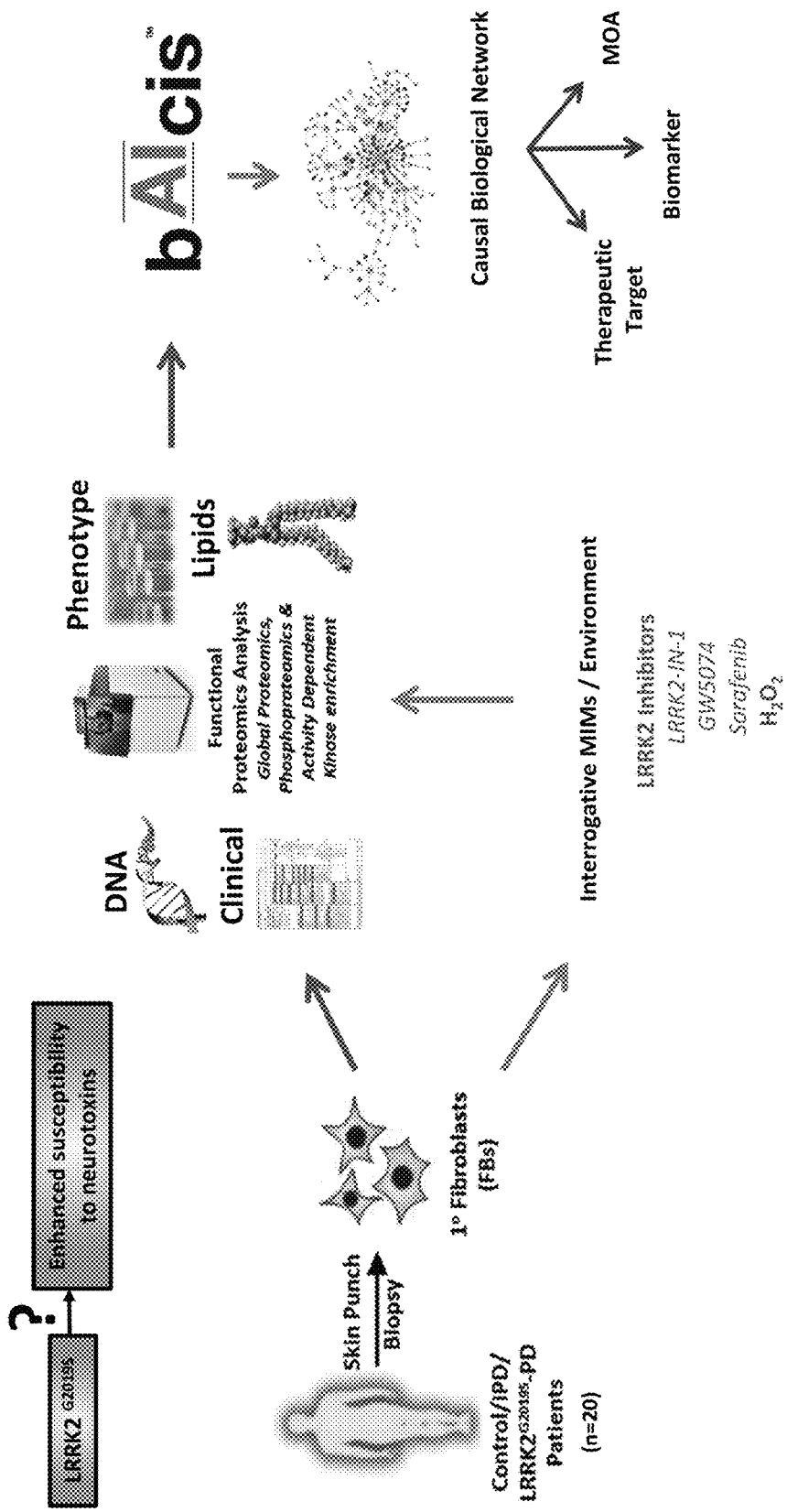
FIG. 2 is a flowchart illustrating the use of the Interrogative Biology® Platform to elucidate downstream mediators of LRRK2-associated PD.
Figure 3:
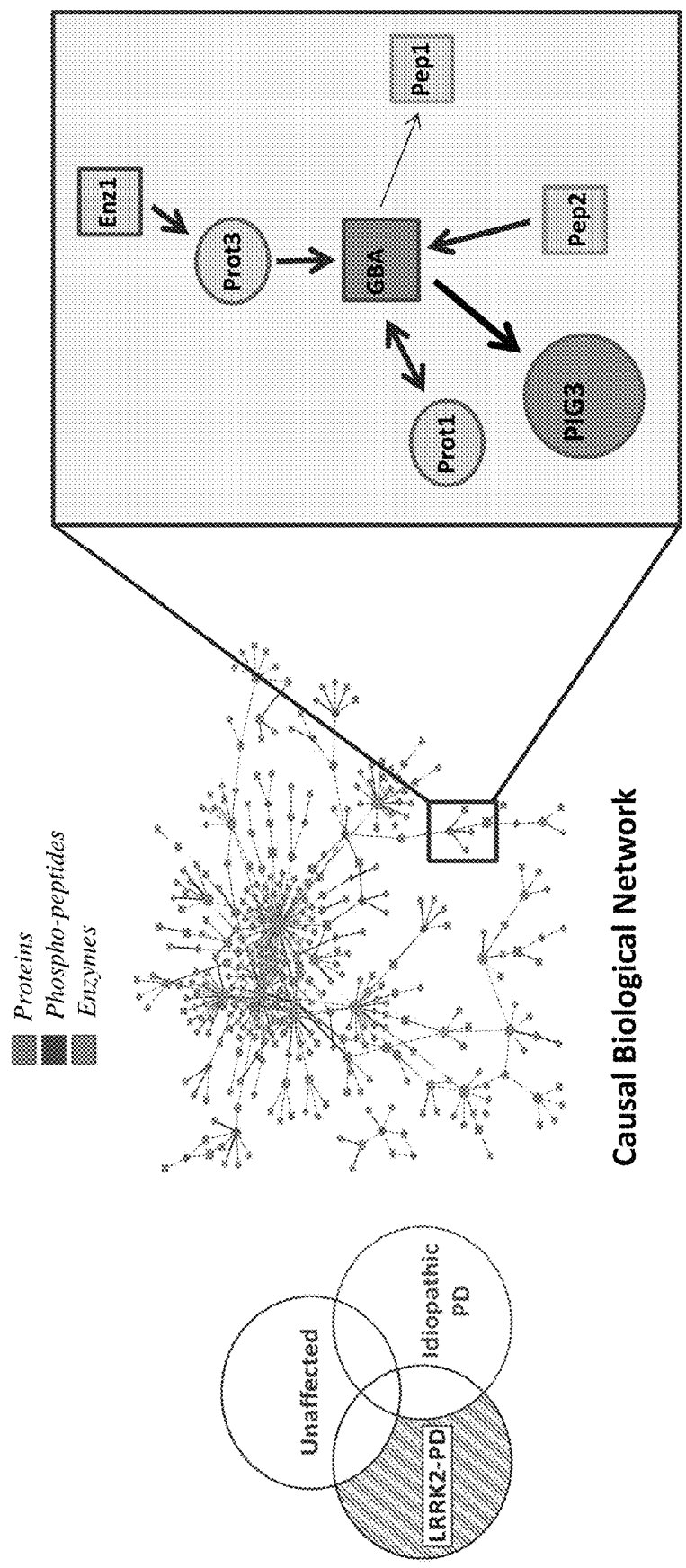
FIG. 3 is a schematic illustration of the identification of a novel biological relationship between GBA and the apoptosis modulator, PIG3, in LRRK2-mediated PD.

A discovery platform technology (FIG. 1) was used to identify the mechanistic link between the LRRK2 mutation and the development of PD pathology (FIGS. 2 and 3). Quinone oxidoreductase (PIG3 or TP53I3) was identified through this discovery platform technology as a therapeutic target for treating and/or preventing the development of pathology associated with PD. The discovery platform also identified beta-glucocerebrosidase (GBA) as being involved in the development of PIG3 associated PD pathology.

Figure 4:
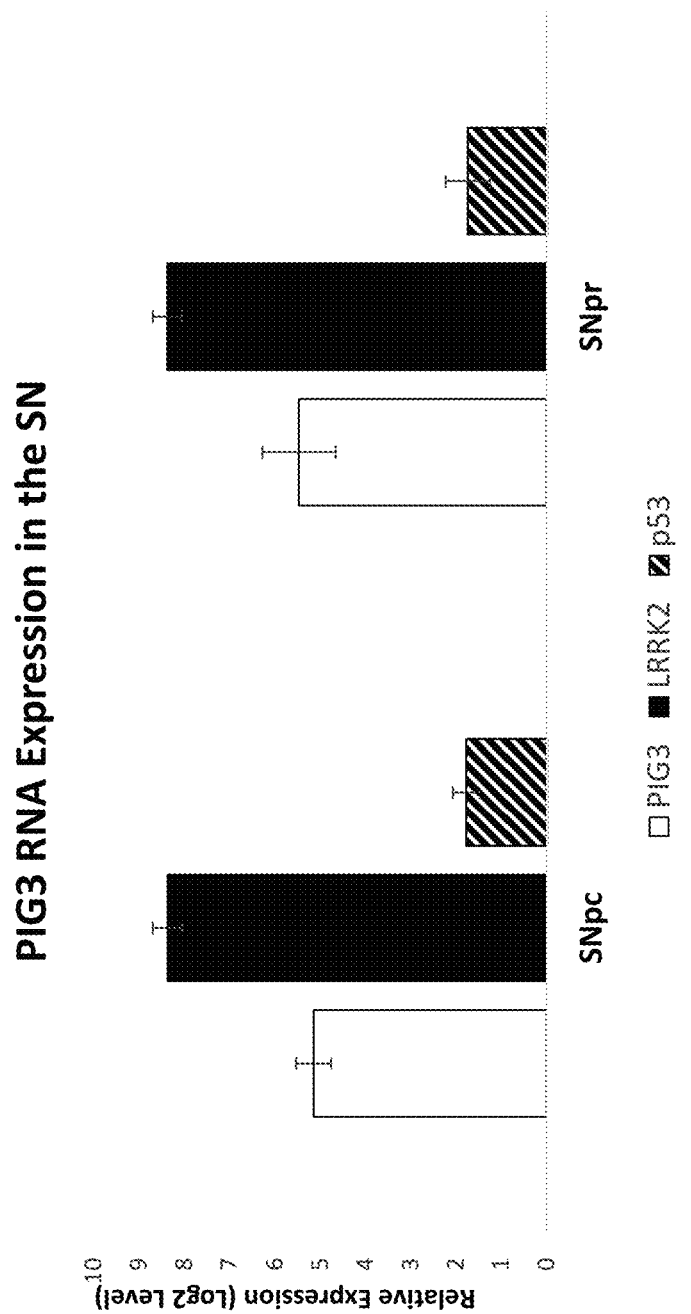
FIG. 4 is a bar graph showing relative expression of PIG3, LRRK2 and p53 in Substantia Nigra pars compacta (SNpc) and Substantia Nigra pars reticulata (SNpr). The bar graph is reproduced from Hawrylycz et al., *Nature* 2012, 489, 391-9.
Figure 5:
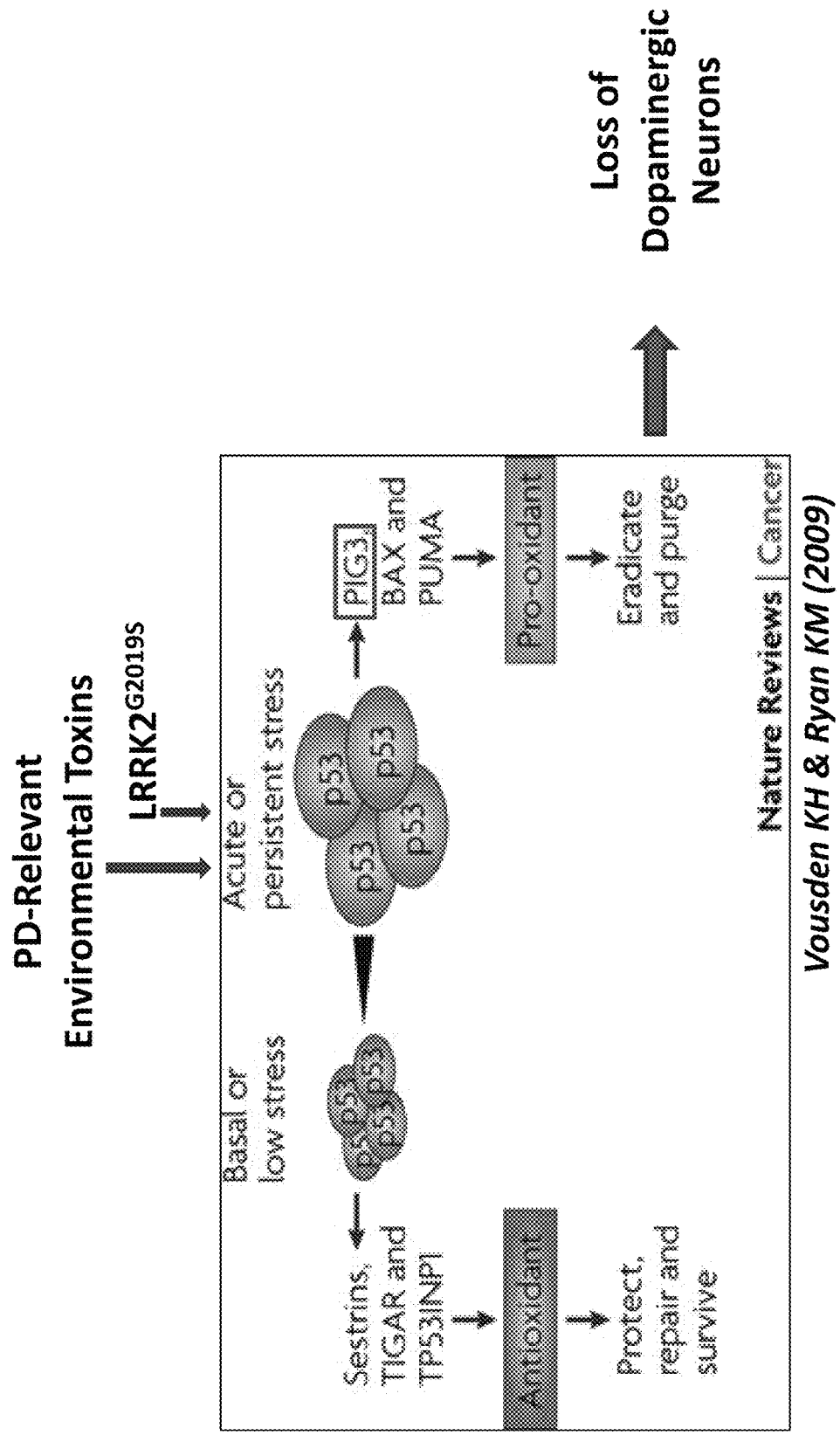
FIG. 5 is a schematic representation of signaling network involved in regulation of oxidative stress by p53. The schematic is reproduced from Vousden and Ryan, *Nature Reviews Cancer* 2009, 9, 691-700.
Figure 6:
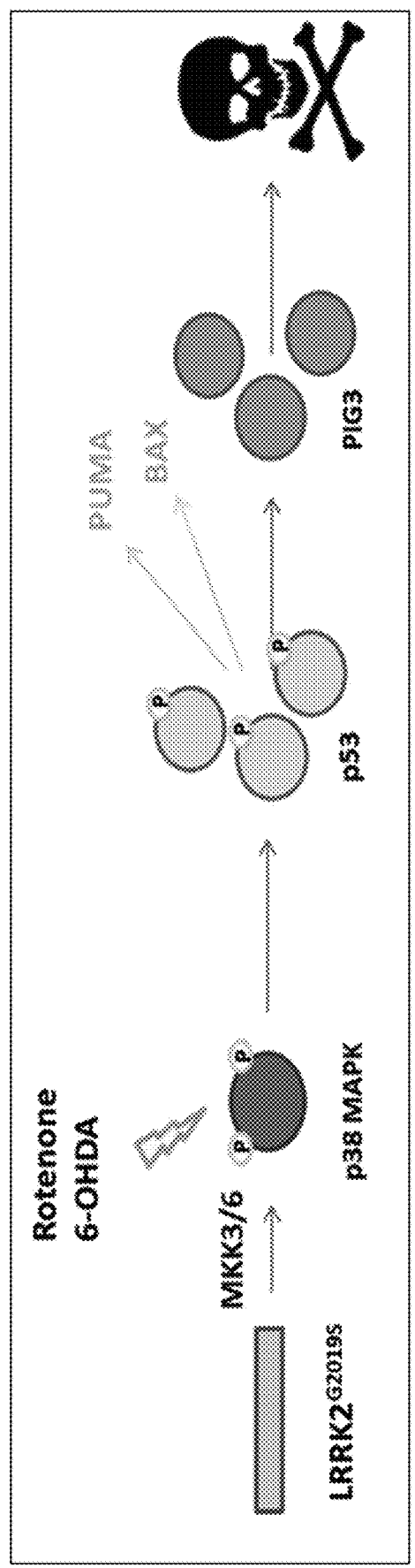
FIG. 6 is a schematic showing the proposed model of neuronal toxicity mediated by PIG3 in dopaminergic neurons in Parkinson's Disease.

The p53-inducible protein 3 (PIG3) is encoded by the TP53I3 gene in humans. The amino acid sequence of human PIG3 may be, e.g., as shown in SEQ ID NO: 1. PIG3 was originally identified through a serial analysis of gene expression in a study designed to identify genes induced by p53 before the onset of apoptosis. Interaction between p53 and PIG3 occurs through binding of p53 to a pentanucleotide microsatellite sequence within the PIG3 promoter that is required for the transcriptional activation of this promoter by p53. The PIG3 amino acid sequence shows significant homology to that of NADH quinine oxidoreductase1 (NQO1), suggesting that, like NQO1, PIG3 contributes to the generation of reactive oxygen species (ROS), which are important downstream mediators of the p53-dependent apoptotic response. Moreover, human cellular apoptosis susceptibility protein (hCAS/CSE1L) interacts with the PIG3 promoter and affects p53-dependent apoptosis by regulating PIG3 expression. As shown in FIG. 4, PIG3, LRRK2 and p53 are expressed in Substantia Nigra pars compacta (SNpc) and Substantia Nigra pars reticulata (SNpr), brain structures implicated in PD (Hawrylycz et al., Nature 2012, 489, 391-9).

Glucocerebrosidase (glucosylceramidase, GCase) is encoded by the beta-glucocerebrosidase (GBA) gene in humans. GCase is a lysosomal enzyme (EC 3.2.1.45) that cleaves glucosylceramide (a monohexosylceramide) into glucose and ceramide. The amino acid sequence of human GCase may be, e.g., as shown in SEQ ID NO: 2. Mutations in the GBA gene are linked to Gaucher disease, which is characterized by the diminished glucocerebrosidase enzymatic activity and associated glucocerebroside accumulation in the spleen, liver and bone marrow.

Glucosylceramide synthase (ceramide glucosyltransferase, GluCer synthase or GCS) is an enzyme (EC 2.4.1.80) that catalyzes production of glucosylceramide from ceramide and glucose. The amino acid sequence of human GluCer synthase may be, e.g., as shown in SEQ ID NO: 3. GCS is encoded in humans by the UDP-glucose ceramide glucosyltransferase gene (UGCG). Synthesis and cleavage of glucosylceramide is illustrated in Scheme 1 below.

Scheme 1.

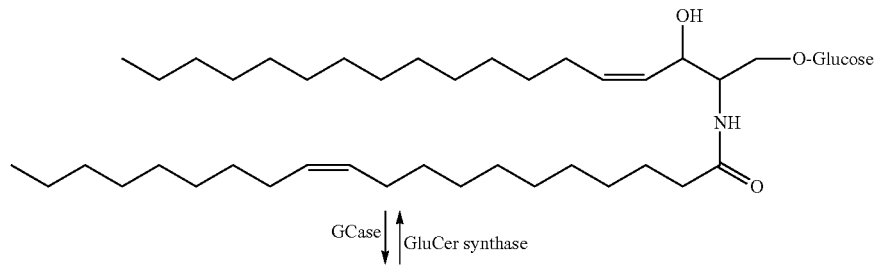

-continued

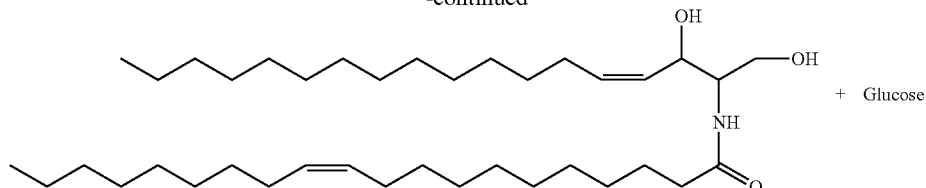

The mechanism by which mutations in GBA may be linked to Parkinson's disease remains to be elucidated. As mutations lead to a reduction in glucocerebrosidase enzymatic activity, and more "severe" mutations in GBA are associated with higher risk for Parkinson's disease compared to "milder" mutations, loss of glucocerebrosidase enzymatic activity may be a pathogenic mechanism. Little is known about glucocerebrosidase enzymatic activity in carriers of specific heterozygous GBA mutations, and there is currently no evidence of sphingolipid accumulation in heterozygotes (as opposed to patients with Gaucher disease); however, increased production of cytosolic reactive oxygen species has been demonstrated in fibroblasts from GBA heterozygotes with and without Parkinson's disease. Interestingly, it was found that carriers of the LRRK2 mutation G2019S have higher glucocerebrosidase enzymatic activity than non-carriers, and even higher than controls without Parkinson's disease (see Alcalay et al., *Brain* 2015, 138, 2648-2658, the entire contents of which are incorporated herein by reference).

The present inventors have demonstrated that in vitro chemical models of Parkinson's Disease are characterized by increased apoptosis and increased PIG3 expression, and siRNA directed against PIG3 (PIG3 siRNA) can significantly reduce cell death in these models. Inhibition of either p38 MAPK or LRRK2 activity, both of which act upstream of p53 in the signal transduction cascade thought to be involved in the PD pathogenesis, exerts a neuroprotective effect by reducing PIG3 expression. On the other hand, it was also demonstrated that overexpression of PIG3 in dopaminergic neurons leads to increased ROS and reduced cell viability. PIG3 was also shown to be upregulated, with the concomitant reduction in cell viability, upon neurotoxin treatment of patient-specific iPS cells (iPSCs). Furthermore, cells isolated from human patients harboring the G2019S mutation in the LRRK2 gene demonstrated chronic activation of the MAPK signaling pathway and increased levels of PIG3 protein.

In summary, the present inventors discovered that the development of PD pathology, e.g., in cells comprising mutations that predispose for the development of PD pathology, e.g., cells with the LRRK2 (G2019S) mutation, is mediated, in part, by PIG3 and involves activation of the MAPK signaling pathway and increased ROS production. Therefore, PIG3 is a viable therapeutic target for PD, and treatment of PD may be achieved by modulating (e.g., inhibiting) the expression or activity of PIG3. The present inventors also discovered that beta-glucocerebrosidase, encoded by the GBA gene, is also involved, along with PIG3, in the development of PD pathology. Without being bound by a specific theory, it is believed that the PIG3 dependent development of PD pathology may involve mediating ROS production.

Accordingly, in some embodiments, the present invention provides methods for treating Parkinson's Disease (PD) that comprise administering to a subject in need thereof a modulator of p53-inducible gene 3 (PIG3), thereby treating the PD in the subject. In some embodiments, PD is an idiopathic PD. In other embodiments, the PD is associated with a genetic mutation that predisposes a subject to developing PD, e.g., a genetic mutation in a glucocerebrosidase (GBA) gene or leucine rich repeat kinase 2 (LRRK2) gene.

PIG3 Modulators

The term "modulator of p53-inducible gene 3", used interchangeably with the term "modulator of PIG3" and the term "PIG3 modulator" encompasses any agent capable of modulating activity of PIG3. A PIG3 modulator can act by any mechanism, e.g., by modulating the expression of PIG3 at the RNA or protein level; by modulating the activity of the PIG3 protein; or by modulating the stability of the PIG3 mRNA or PIG3 protein. In some embodiments, the PIG3 modulator is a PIG3 inhibitor, e.g., a specific PIG3 inhibitor.

In some embodiments, a PIG3 modulator may be an agent that is capable of directly modulating PIG3, i.e., associating with, or binding to, the PIG3 protein or PIG3 mRNA, thereby modulating the expression of PIG3 mRNA or the activity of the PIG3 protein. In other embodiments, the PIG3 modulator may be an agent capable of indirectly modulating PIG3. For example, the PIG3 modulator capable of indirectly modulating PIG3 may modulate, e.g., inhibit, PIG3 through modulation of PIG3's transcription factor, hCAS/CSE1L. This factor associates with a subset of p53 target genes involved in apoptosis. The hCAS/CSE1L transcription factor binds to the PIG3 promoter region. Silencing of hCAS/CSE1L leads to a reduction in PIG3 transcription and to an increased methylation of histone in H3Lys-27 within the PIG3 gene, resulting in reduced apoptosis (Tanaka et al., Cell 2007, 130(4):638-50, the entire contents of which are incorporated herein by reference).

A PIG3 modulator, e.g., a PIG3 inhibitor, may be selected from the group consisting of a small organic molecule, a small inorganic molecule; a monosaccharide; a disaccharide; a trisaccharide; an oligosaccharide; a polysaccharide; a peptide; a protein; a peptide analog; a peptide derivative; a peptidomimetic; an antibody (polyclonal or monoclonal); an antigen binding fragment of an antibody; a nucleic acid, e.g., an oligonucleotide, an antisense oligonucleotide, siRNAs, shRNAs, a ribozyme, an aptamer, microRNAs, a pre-microRNAs, iRNAs, plasmid DNA (e.g. a condensed plasmid DNA), modified RNA, a nucleic acid analog or derivative; and any combinations thereof. The nucleic acid may comprise one or more unnatural nucleotides. The peptide or the protein may comprise one or more unnatural amino acids.

In some embodiments, a PIG3 modulator may be a small molecule. As used herein, the term "small molecule" can refer to a compound that contains several carbon-carbon bonds, and has a molecular weight of less than 5000 Daltons (5 kD), preferably less than 3 kD, still more preferably less than 2 kD, and most preferably less than 1 kD. In some cases, the small molecule may have a molecular weight equal to or less than 700 Daltons. In some embodiments, because PIG3 displays significant homology to a human NADP quinone oxidoreductase, a small molecule PIG3 modulator useful in the methods of the present invention may be, e.g., a small molecule capable of modulating, e.g., inhibiting, a human NADP quinone oxidoreductase. Exemplary non-limiting small molecule agents known to inhibit a human NADP quinone oxidoreductase are described in Kapinya et al., *Journal of Neurochemistry* 2003, 84, 1028-1039 (the entire contents of which are incorporated herein by reference) and include, e.g., Dicoumarol (dicumarol), cibacron blue or chrysin, with structures as shown below:

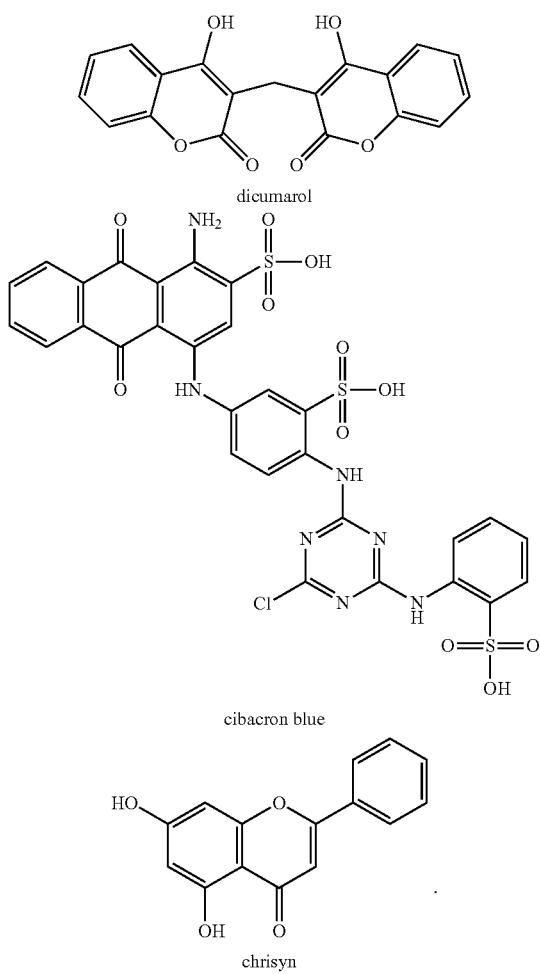 [SMILES: O=c1oc2ccccc2c(O)c1Cc1c(O)c2ccccc2oc1=O ; Nc1c(S(=O)(=O)O)cc(Nc2ccc(Nc3nc(Cl)nc(Nc4ccccc4S(=O)(=O)O)n3)c(S(=O)(=O)O)c2)c2c1C(=O)c1ccccc1C2=O ; O=c1cc(-c2ccccc2)oc2cc(O)cc(O)c12]

In some embodiments, the PIG3 modulator useful in the methods of the present invention may be a peptide or a polypeptide. The term "peptide" is used herein in its broadest sense to refer to compounds containing amino acids, amino acid equivalents or other non-amino groups, while still retaining the desired functional activity of a peptide. Peptide equivalents may differ from conventional peptides by the replacement of one or more amino acids with related organic acids (such as PABA), amino acids or the like or the substitution or modification of side chains or functional groups. The peptides may be linear or cyclic. A peptide may be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid.

In some embodiments, a PIG3 modulator useful in the methods of the present invention may also be a protein or an antibody, e.g., a polyclonal or a monoclonal antibody. The term "monoclonal antibody" or "monoclonal antibody composition", as used herein, refers to a population of antibody molecules that contain only one species of an antigen binding site capable of immunoreacting with a particular epitope. Antibodies useful for the present invention include antibodies that bind to PIG3. Antibodies can be obtained from commercial sources or produced using known methods.

For example, monoclonal antibodies may be prepared by immunizing a suitable subject with a protein of the invention as an immunogen. The antibody titer in the immunized subject may be monitored over time by standard techniques, such as with an enzyme linked immunosorbent assay (ELISA) using immobilized polypeptide. At an appropriate time after immunization, e.g., when the specific antibody titers are highest, antibody-producing cells may be obtained from the subject and used to prepare monoclonal antibodies (mAb) by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., *John Wiley & Sons*, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against PIG3 may be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Recombinant antibodies that specifically bind PIG3 may also be used in the methods of the invention. In preferred embodiments, the recombinant antibody specifically binds PIG3 or a fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They may be produced by techniques known in the art, for example using methods described in Ladner et al., U.S. Pat. No. 4,946,778 (which is incorporated herein by reference in its entirety); Bird et al., (1988) *Science* 242:423-426; Whitlow et al., (1991) *Methods in Enzymology* 2:1-9; Whitlow et al., (1991) *Methods in Enzymology* 2:97-105; and Huston et al., (1991) *Methods in Enzymology Molecular Design and Modeling: Concepts and Applications* 203:46-88. Multispecific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) *Proc. Natl. Acad. Sci. USA* 90:6444-6448; Whitlow et al., (1994) *Protein Eng.* 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule (see, e.g., Queen, U.S. Pat. No. 5,585,089, which is incorporated herein by reference in its entirety). Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

More particularly, humanized antibodies may be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of PIG3. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies may be engaged to provide human antibodies directed against a selected antigen using technology similar to that described above.

Completely human antibodies which recognize a selected epitope may be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

Examples of PIG3 binding antibodies known in the art include, but are not limited to, commercially available anti-PIG3 antibodies, such as ab64798 and ab226975 (Abcam); A-5, 10A2, sc-30068, H-300 (Santa Cruz Biotechnology); AT1C9 and N1C3 (GeneTex); TP5313 Antibody Picoband (Bosterbio); NBP2-22591 (Novus Biologicals); and Leu265 (Isbio). Specificity in the association of, e.g., the anti-PIG H-300 antibody is demonstrated in Lee et al., *Oncogene* 2010, 29, 1431-1450. Antibody PIG3 modulators, e.g., antibody PIG3 inhibitors, that are useful in the methods of the present invention may be reactive with the active site of PIG3, to inhibit its enzyme activity. An inactive PIG3 does not generate reactive oxygen species, as demonstrated in Porte et al., *J. Biol. Chem.* 2009, 284, 17194-17205.

The PIG3 modulator useful in the methods of the present invention may also be a nucleic acid. As used herein, the term "nucleic acid" or "oligonucleotide" refers to least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. An RNA molecule may be selected from the group consisting of an mRNA, an RNAi, an siRNA, an shRNA, a microRNA, an isRNA, a lncRNA and an antisense RNA.

A nucleic acid PIG3 modulator, e.g., a nucleic acid PIG3 inhibitor, may be any nucleic acid based agent that modulates, e.g., decreases the expression of PIG3 by hybridizing with at least a portion of the mRNA transcript from the PIG3 gene to result in a modulation, e.g., a decrease in the expression of the PIG3. A nucleic acid PIG3 modulator may include, for example, a single stranded nucleic acid molecule, e.g., an antisense nucleic acid, or a double stranded nucleic acid molecule, such as siRNA, shRNA or dsiRNA as described, e.g., in US 2007/0104688, the entire contents of which are incorporated herein by reference. Double stranded nucleic acid molecules may be designed to be double stranded over at least 12, and preferably at least 15 nucleotides. A double stranded nucleic acid molecule may be a single nucleic acid strand designed to hybridize to itself, e.g., an shRNA.

It is understood that a nucleic acid PIG3 modulator may be administered as an isolated nucleic acid. Alternatively, the nucleic acid PIG3 modulator may be administered as an expression construct to produce the inhibitor in the cell. In certain embodiments, the nucleic acid PIG3 modulator includes one or more chemical modifications to improve the activity and/or stability of the nucleic acid PIG3 modulator. Such modifications are well known in the art. The specific modifications to be used will depend, for example, on the type of the nucleic acid PIG3 modulator.

Exemplary publications describing nucleic acid agents, e.g., antisense nucleic acids, chemical modifications, and therapeutic include, for example, U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 is related to methods of treating patients by administering single-stranded chemically modified RNA-like compounds; and U.S. Pat. No. 7,432,249 is related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in this paragraph are expressly incorporated herein by reference in their entirety.

Nucleic acid PIG3 modulators, e.g., nucleic acid PIG3 inhibitors, that are useful in the method of the present invention may include natural (i.e., A, G, U, C, or T) or modified (7-deazaguanosine, inosine, etc.) bases. In addition, the bases in nucleotide may be joined by a linkage other than a phosphodiester bond, so long as it does not interfere with hybridization. Thus, inhibitory nucleic acids may be peptide nucleic acids in which the constituent bases are joined by peptide bonds rather than phosphodiester linkages. The inhibitory nucleic acids may be prepared by converting the RNA to cDNA using known methods (see, e.g., Ausubel et. al., *Current Protocols in Molecular Biology Wiley* 1999). The inhibitory nucleic acids can also be cRNA (see, e.g., Park et. al., (2004) Biochem. Biophys. Res. Commun. 325(4):1346-52).

Nucleic acid PIG3 modulators may include one or more chemical modifications to improve their stability and to modulate their pharmacokinetic and pharmacodynamic properties. Exemplary non-limiting modifications on the nucleotides may include, e.g., LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof.

Nucleic acid PIG3 modulators useful in the methods of the present invention may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid modulator including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

Other modifications that may be present in the nucleic acid PIG3 modulator useful in the methods of the present invention may include modified bases (or modified nucleoside or modified nucleotides) that are variations of standard bases, sugars and/or phosphate backbone chemical structures occurring in ribonucleic (i.e., A, C, G and U) and deoxyribonucleic (i.e., A, C, G and T) acids. Included within this scope are, for example: Gm (2'-methoxyguanylic acid), Am (2'-methoxyadenylic acid), Cf (2'-fluorocytidylic acid), Uf (2'-fluorouridylic acid), Ar (riboadenylic acid). The nucleic acid PIG3 modulator may also include cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine), 5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine. The nucleic acid PIG3 modulator may also include guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The nucleic acid PIG3 modulator may also include adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included are uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl)uracil, 5-methylaminomethyluracil, 5-propynyl uracil, 6-azouracil, or 4-thiouracil.

Examples of other modified base variants known in the art include, without limitation, e.g., 4-acetylcytidine, 5-(carboxyhydroxylmethyl) uridine, 2'-methoxycytidine, 5-carboxymethylaminomethyl-2-thioridine, 5-carboxymethylaminomethyluridine, dihydrouridine, 2'-O-methylpseudouridine, b-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, b-D-mannosylqueosine, 5-methoxycarbonylmethyluridine, 5-methoxyuridine, 2-methylthio-N6-isopentenyladenosine, N-((9-b-D-ribofuranosyl-2-methylthiopurine-6-yl)carbamoyl)threonine, ribofuranosylpurine-6-yl)N-methyl-carbamoyl)threonine, urdine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, D-ribofuranosylpurine-6-yl)carbamoyl) threonine, 2'-O-methyl-5-methyluridine, 2'-O-methyluridine, and wybutosine, 3-(3-amino-3-carboxypropyl)uridine.

Also included are the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941, each of which is incorporated herein by reference in its entirety. Examples of modified nucleoside and nucleotide sugar backbone variants known in the art include, without limitation, those having, e.g., 2' ribosyl substituents such as F, SH, SCH$_3$, OCN, Cl, Br, CN, CF$_3$, OCF$_3$, SOCH$_3$, SO$_2$, CH$_3$, ONO$_2$, NO$_2$, N$_3$, NH$_2$, OCH$_2$CH$_2$OCH$_3$, O(CH$_2$)$_2$ON(CH$_3$)$_2$, OCH$_2$OCH$_2$N(CH$_3$)$_2$, O(C$_{1-10}$ alkyl), O(C$_{2-10}$ alkenyl), O(C$_{2-10}$ alkynyl), S(C$_{1-10}$ alkyl), S(C$_{2-10}$ alkenyl), S(C2-10 alkynyl), NH(C1-10 alkyl), NH(C$_{2-10}$ alkenyl), NH(C2-10 alkynyl), and O-alkyl-O-alkyl. Desirable 2' ribosyl substituents include 2'-methoxy (2'-OCH$_3$), 2'-aminopropoxy (2' OCH$_2$CH$_2$CH$_2$NH$_2$), 2'-O-allyl (2'-CH$_2$—CH=CH$_2$), 2'-O-allyl(2'-O—CH$_2$—CH=CH$_2$), 2'-amino (2'-NH$_2$), and 2'-fluoro (2'-F). The 2'-substituent may be in the arabino (up) position or ribo (down) position.

In the art, inhibition of the expression of PIG3 was accomplished by shRNA, siRNA and lentivirus-based approaches. These tools were used for silencing of PIG3 in human carcinoma cells (Park et al., *Korean J Physiol Pharmacol* 2017, 21(2): 267-273), lung adenoma cells (Jiang Y et al., *Tumour Biol.* 2016, 37(3):3785-95.) and in gliablastoma cells (Quan et al., *Tumour Biology* (2017): In press.). Exemplary shRNA sequences that are known to silence PIG3 include 5'-ccggatggctggagctatt-3' (SEQ ID NO: 5) and 5'-tgttcaggctggagactat-3' (SEQ ID NO: 6) (Quan et al., *Tumour Biology* (2017): In press.), 5'-AAAUGUUCAGGCUGGAGACUA-3' (SEQ ID NO: 7) (Park et al., *Korean J Physiol Pharmacol* 2017, 21(2): 267-273), as well as other PIG3-specific silencing reagents, e.g., available from Santa Crux Biotechnology.

Assays suitable for evaluating the level and/or activity of a PIG3 modulator, e.g., a PIG3 inhibitor, may be easily determined by one of ordinary skill in the art. For example such assays may involve measuring PIG3 expression by measuring the amount of PIG3 mRNA using quantitative PCR (qPCR). Such assays may also involve measuring the amount of PIG3 protein, e.g., by using immunoblotting. Furthermore, assessment of PIG3 activity can be accomplished in cellular models by estimating relative ROS production and the downstream induction of cell death. PIG3-mediated reduction of quinones may also serve as a direct and relevant intracellular readout for PIG3 activity. Others have demonstrated direct interactions between PIG3 and other proteins (e.g., catalase; Kang et al., Cell Death Differ. 2013, 20:117-129) that may be monitored to assess the disease modifying potential of a PIG3 modulator.

As used herein, modulation, in the expression, activity or stability of PIG3 is understood to include a change, e.g., a decrease, in expression or activity of the PIG3. For example, expression, activity or stability of PIG3 may be changed, e.g., reduced, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In one embodiment, expression of PIG3 may be changed, e.g., reduced, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In another embodiment, the activity of PIG3 may be changed, e.g., reduced, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In one embodiment, the stability of PIG3 may be changed, e.g., reduced, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%.

Administration of the PIG3 Modulator

The methods for treating PD provided by the present invention comprise administering a PIG3 modulator to a subject in need thereof. Techniques and dosages for administration vary depending on the type of compound (e.g., a small molecule, an antibody, or a nucleic acid) and are well known or may be readily determined by those skilled in the art.

Therapeutic agents of the present invention, i.e., PIG3 modulators, may be administered alone or as a part of a pharmaceutical composition that may comprise a pharmaceutically acceptable diluent, carrier, or excipient, in unit dosage form. Administration of a PIG3 modulator, e.g., a PIG3 inhibitor, may be parenteral, intravenous, subcutaneous, oral, topical, or local. Administration of the PIG3 modulator useful in the methods of the present invention may be performed by one person or by a number of people working in concert. Administering a therapeutic agent, e.g., a PIG 3 modulator may include, for example, prescribing the therapeutic agent to be administered to a subject and/or providing instructions, directly or through another, to take a specific therapeutic agent, either by self-delivery, e.g., as by oral delivery, subcutaneous delivery, intravenous delivery through a central line, etc, or for delivery by a trained professional, e.g., intravenous delivery, intramuscular delivery, etc.

The pharmaceutical composition comprising a PIG3 modulator may be in the form of a pill, tablet, capsule, liquid, or sustained release tablet for oral administration; or a liquid for intravenous, subcutaneous, or parenteral administration; or a polymer or other sustained release vehicle for local administration.

Methods for making pharmaceutical compositions are well known in the art and are described, e.g., in "Remington: The Science and Practice of Pharmacy" (20th ed., ed. A. R. Gennaro, 2000, Lippincott Williams & Wilkins, Philadelphia, Pa.). Pharmaceutical compositions for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the therapeutic agents, e.g., PIG3 modulators. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the PIG3 modulator to be administered, and the route of administration.

The PIG3 modulator may also be optionally administered as a pharmaceutically acceptable salt, such as a non-toxic acid addition salt or a metal complex that are commonly used in the pharmaceutical industry. Examples of acid addition salts include salts of organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acid and the like; polymeric acids, such as tannic acid, carboxymethyl cellulose, and the like; and inorganic acids such as hydrochloric, hydrobromic, sulfuric, phosphoric acid, and the like. Metal complexes include zinc, iron, and the like.

For oral administration, PIG3 modulators may be administered as a part of a tablet or a capsule. Formulations for oral use include tablets containing the active ingredient, i.e., the PIG3 modulator, in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Formulations for oral use may also be provided as chewable tablets, or as hard gelatin capsules in which the active ingredient is mixed with an inert solid diluent, or as soft gelatin capsules in which the active ingredient is mixed with water or an oil medium.

The dosage and the timing of administering the compound depend on various clinical factors including the overall health of the subject and the severity of the symptoms of PD.

Treatment of Parkinson's Disease

The present invention provides methods for treating Parkinson's Disease (PD) associated with a genetic mutation in a glucocerebrosidase (GBA) gene or leucine rich repeat kinase 2 (LRRK2) gene. The methods comprise administering to a subject in need thereof a modulator of p53-inducible gene 3 (PIG3), thereby treating the PD in the subject.

The present invention is useful for treating PD associated with a LRRK2 mutation. LRRK2, also known as dardarin (from the Basque word "dardara" which means trembling), is encoded in humans by the PAK8 gene. LRRK2 is an unusually large protein (2527 amino acids) classified as a member of the ROCO superfamily which is characterized by the presence of tandem Ras of complex (Roc) G-domain, kinase domains and carboxy-terminal of Roc (COR) sequence which links them. The human sequence of LRRK2 is provided as SEQ ID NO: 4.

PD associated with any mutation in LRRK2 gene is encompassed by the methods of the present invention. Non-limiting examples of pathogenic mutations in the LRRK2 gene that have been associated with autosomal dominant, late-onset Parkinson's disease include the G2019S mutation, the R1441C mutation, the R1441G mutation, the R1441H mutation, the Y1699C mutation, the I2020T mutation and the N1437H mutation.

In a specific embodiment, the mutation in the LRRK2 gene is the G2019S mutation. The G2019S mutation is the most common mutation in familial PD cases and was estimated by the international LRRK2 consortium to represent 1% of sporadic and 4% of familial PD patients worldwide. Notably, the frequency of this mutation varies greatly among ethnic groups and geographic origins. In fact, the highest frequencies are observed in North African countries with 30-40% and Ashkenazi Jews with 10-30%. In Europe, the frequency of G2019S mutation appears to be relatively higher in southern countries particularly in Portugal and Spain with 2-14% of PD cases, than in northern countries with 0-3%, suggesting a European north-south gradient. The presence of G2019S in PD patients is very rare in Asian populations with a frequency less than 0.1% in China, Japan, Korea, and India, whereas it can reach 1-3% in white North American population.

In some embodiments, the methods of the present invention comprise the step of identifying a subject as having a genetic mutation in the LRRK2 gene. Methods of identifying mutations, e.g., specific mutations as described above, are known to one of ordinary skill in the art.

Typical signs and symptoms of PD, i.e., cardinal symptoms, may include at least one symptom from of the following:

a) a tremor, or shaking, which usually begins in a limb, often hand or fingers. The tremor associated with PD may include a back-and-forth rubbing of the thumb and forefinger, known as a pill-rolling tremor, and a tremor of the hand when it is relaxed (at rest);

b) slowed movement (bradykinesia);

c) rigid muscles;

d) impaired posture and balance;

e) loss of automatic movements;

In addition, "non-motor symptoms" or "dopamine-non-responsive" symptoms, are also common in subject in PD and may include any of the following:

f) cognitive impairment;

g) mood disorders, e.g., depression and anxiety;

h) sleeping problems, including REM Sleep Disorder, where individuals act out their dreams;

i) low blood pressure when standing;

j) constipation;

k) speech and swallowing problems; and l) unexplained pains, drooling and smell loss.

Clinically, the presentation of typical LRRK2-associated PD is indistinguishable from idiopathic PD with late-onset, levodopa-responsive parkinsonism. In some cases, however, atypical features have been observed, including early disease onset; muscular atrophy (amyotrophy); dementia; hallucinations; delusions; and uncontrollable muscle contraction (dystonia) of lower extremities. Distinctive neuropathological features have also been observed in LRRK2-associated PD and include Lewy body PD to nigral degeneration without distinctive histopathology, or tau-positive neurofibrillary tangle pathology.

In accordance with the methods of the present invention, a PIG3 modulator is administered to a subject in need thereof for treating PD associated with a mutation in a GBA gene or an LRRK2 gene. As used herein, the term "subject" includes human and non-human animals, such as veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, reduction, alleviation or amelioration of one or more signs or symptoms of PD as described above; diminishing the extent of PD, maintaining stability (i.e., not worsening) of PD, amelioration or palliation of the disease state. As used herein, treatment can include one or more of reduction, alleviation or amelioration of the cardinal or non-motor symptoms of PD as described above, e.g., reduction, alleviation or amelioration of tremor, bradykinesia, muscle rigidity, reduction in speech and swallowing problems, etc. In one embodiment, the treatment may also include inhibiting and slowing the progression of PD.

Treatment does not need to be curative. Treatment outcomes need not be determined quantitatively. However, in certain embodiments, treatment outcomes can be quantitated by following the longitudinal course of PD, using, e.g., the Unified Parkinson's Disease Rating Scale (UPDRS), or a revised UPDRS, knowns as MDS-UPDRS. The UPDRS is a scoring system most commonly used for clinical evaluation of Parkinson's disease. It contains 42 items that are evaluated by interview with the subject and clinical observation. A total of 199 point are possible on the UPDRS scale, with 199 representing the worst disability and 0 representing no disability. UPDRS comprises the following sections:

Part I: evaluation of mentation, behavior, and mood;
Part II: self-evaluation of the activities of daily life (ADLs) including speech, swallowing, handwriting, dressing, hygiene, falling, salivating, turning in bed, walking, and cutting food;
Part III: clinician-scored monitored motor evaluation;
Part IV: complications of therapy;
Part V: Hoehn and Yahr staging of severity of Parkinson's disease; and
Part VI: Schwab and England ADL scale.

These are evaluated by interview and clinical observation. Some sections require multiple grades assigned to each extremity. The revised UPDRS retains the four-scale structure of the original UPDRS, with a reorganization of the various subscales. The scales are titled; (1) nonmotor experiences of daily living (13 items), (2) motor experiences of daily living (13 items), (3) motor examination (18 items), and (4) motor complications (six items). Each subscale has 0-4 ratings, where 0=normal, 1=slight, 2=mild, 3=moderate, and 4=severe.

The UPDRS or MDS-UPDRS may be used to follow the progression of a persons Parkinson's disease or to measure benefits from a therapy, e.g., a therapy that comprises administering a PIG3 inhibitor.

In some embodiments, administering of a PIG3 modulator, e.g., PIG3 inhibitor, to a subject in accordance with the methods of the invention results in inhibition or in slowing down the PD progression in the subject. Specifically, in some embodiments, administering of a PIG3 inhibitor to a subject results in a substantially no increase of the UPDRS score in the subject over a period of time, e.g., over 1 week, 2 weeks, 3 weeks, 1 month, 2 months, 3 months, 6 months, 9 months, 1 year, 2 years, 3 years or 5 years. In some embodiments, administering of a PIG3 inhibitor to a subject results in a decrease of the UPDRS score in the subject over a period of time, e.g., over 1 week, 2 weeks, 3 weeks, 1 month, 2 months, 3 months, 6 months, 9 months, 1 year, 2 years, 3 years or 5 years.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

In some embodiments, PIG3 modulators may be administered to a subject in accordance with the methods of the present invention as a monotherapy. In other embodiments, PIG3 modulators may be administered in combination with one or more medications or therapies used for treating PD. Non-limiting examples of medications used for treating PD include levodopa (alone or combined with carbidopa); dopamine agonists, such as pramipexole (Mirapex), ropinirole (Requip) and rotigotine (Neupro), and apomorphine (Apokyn); monoamine oxidase B (MAO-B) inhibitors, such as selegiline (Eldepryl, Zelapar) and rasagiline (Azilect); catechol-O-methyltransferase (COMT) inhibitors, such as entacapone (Comtan) and tolcapone (Tasmar); anticholinergics, such as benztropine (Cogentin) and trihexyphenidyl; and amantadine. In addition, the PIG3 modulators may be administered to a subject in accordance with the methods of the present invention prior or after a surgical procedure used for treating PD symptoms, such as deep brain stimulation (DBS).

Combination Therapy

In some embodiments, the present invention also provides methods for treating

Parkinson's Disease (PD) associated with a genetic mutation in a GBA gene by employing a combination therapy. The methods comprise administering to the subject a PIG3 modulator in combination with a GCS modulator. As is evident from Scheme 1, the product of the GBA gene, GCase, catalyzes cleavage of glucosylceramide (a monohexosylceramide) into glucose and ceramide. An inactivating mutation in the GBA gene results in accumulation of glucosylceramide, which leads to further toxicity. Accumulation of glucosylceramide may be prevented by modulating, e.g., inhibiting, the activity of GCS which produces glucosylceramide. Administering a PIG3 modulator in combination with a GCS modulator, results in combined modulation of GCS and PIG3 activity to effectively treat PD in a subject with a GBA mutation.

The term "GCS modulator", used interchangeably herein with the terms "modulator of glucosylceramide synthase", "glucosylceramide modulator" and "GluCer synthase modulator" encompasses any agent capable of modulating activity of GCS. A GCase modulator can act by any mechanism, e.g., by modulating the expression of the UDP-glucose ceramide glucosyltransferase (UGCG) gene that encodes GCS at the RNA or protein level; by modulating the activity of the GCS; or by modulating the stability of the GCS mRNA or GCS protein. In some embodiments, the GCS modulator is a GCS inhibitor.

Any known GCS modulator is contemplated for use in the methods of the present invention. Non-limiting examples of GCase modulators that may be used in the methods of the present invention include (±)-threo-1-Phenyl-2-decanoylamino-3-morpholino-1-propanol hydrochloride (or PDMP hydrochloride); (1R,2R)-nonanoic acid[2-(2',3'-dihydrobenzo [1, 4] dioxin-6'-yl)-2-hydroxy-1-pyrrolidin-1-ylmethyl-ethyl]amide (Genz-123346); EXEL-0346 as described in Richards et al., *J. Med. Chem.* 2012, 55(9), 4322-4335; Miglustat (OGT 918, N-butyl-deoxynojirimycin); Eliglustat (Cerdelga); and compounds described in U.S. Pat. No. 9,139,580, the entire contents of which are hereby incorporated herein by reference; and compounds GZ/SAR402671 and GZ667161.

EXAMPLES

Example 1: Identification of GBA and PIG3 as Therapeutic Targets for PD

In this example, the Interrogative Biology™ Platform illustrated in FIG. 1 and described in detail at least in international Publication Nos. WO 2012/119129 and WO2013/151577, the entire contents of each of which are hereby incorporated herein by reference, was used to study Parkinson's Disease. The technology utilized proteomics techniques for measuring protein activity related to pathogenesis of Parkinson's Disease and the direct effects of that activity on the proteome, thereby providing a system that can be used to understand causal relationships between various proteins in the context of global changes in the cellular proteome in Parkinson's Disease.

In a typical experiment, a model is first established in accordance with the platform technology, in which cells representative of Parkinson's Disease are interrogated by exposure to an environmental perturbation. A control is provided for comparison. Second, enzyme activity and its downstream effects are tracked in the context of global proteomic changes by analyzing (i) global enzymatic activity, (ii) the specific effect of the enzymatic activity on the proteome (e.g., the metabolites/substrates of the enzymatic activity), and (iii) the global effect on the cellular proteome. Third, the datasets are analyzed in accordance with the platform technology to identify modulators of interest. For example, a model of PD may be interrogated by a known PD agent, and the effects of this perturbation to the system on the global kinase activity may be analyzed, along with the resulting effects on the phosphoproteome and whole proteome. Subsequently, comparative proteomics, phosphoproteomics and/or enzyme activity data are integrated into the AI based informatics platform. Causal networks of protein interaction, including from a functional stand point, e.g., kinase/enzyme activity and potential targets that kinases can phosphorylate, are then generated. In addition, using cellular functional read out, enzymes/kinases that modulate phosphorylation of targets and mechanistically drive pathophysiological cellular behavior can be determined (FIG. 2).

This experiment utilized samples from a total of six patients. The patients represented three groups, with 1 male and 1 female in each group. The first group included two patients with idiopathic PD; the second group included two patients with LRRK2-mediated PD; and the third group included two healthy controls. The samples, which were fibroblasts, were interrogated by exposure to an environmental perturbation. Specifically, treatments included Sorafenib (a global kinase inhibitor), GW5074 (an inhibitor of the MAPK signaling pathway), LRRK2-IN-1 (LRRK2 specific inhibitor) and $H_2O_2$. Treatments with each of Sorafenib, GW5074 and LRRK2-IN-1 were carried out at the concentrations of 50 nM and 100 nM for 90 minutes or 6 hours. Treatment with $H_2O_2$ was carried out at the $H_2O_2$ concentration of 10 μM and 100 μM for 90 minutes. Subsequently, to interrogate protein activity, proteins with enzymatic/signaling activity were enriched from the cell lysates using ATP- and ADP-affinity probes and analyzed by mass spectrometry. In parallel, phosphopeptides were analyzed after enrichment from the cell lysates using a $TiO_2$ probe. In addition total proteomics analysis was also performed.

Bayesian network analysis and downstream differential network analysis were performed as follows: Individual Normal fibroblast, idiopathic PD fibroblast and LRKK2 PD fibroblast (including treated and untreated) networks were generated using RIMBAnet. Subsequently, PD-specific delta networks were generated for both the LRRK2 PD and idiopathic PD cell models by producing a differential network of the LRRK2-PD vs. Normal network (LRRK2-PD specific network) and a differential network of the idiopathic PD vs. Normal network (idiopathic PD specific network). In order to identify causal relationships unique to LRRK2-PD, a second differential was performed between the LRRK2-PD specific delta network and the idiopathic PD specific delta network to obtain a network (delta-delta) unique to LRRK-2 PD (LRRK2-PD unique).

As illustrated in FIG. 3, this study identified the apoptosis modulator PIG3 as a secondary node of activity in the LRRK2-PD unique network, indicating that it can be a target for PD therapy. Further, GBA was identified as a hub of activity directly causally connected to PIG3 in the network unique to LRRK-2 PD. Thus, this study also identified a novel causal relationship between PIG3 and GBA in LRRK2-mediated PD. Finally, PIG3 was also present in the single delta idiopathic PD specific network (data not shown), further indicating that PIG 3 is a target for PD therapy.

Example 2: PIG3 Expression is Associated with Rotenone-Induced Apoptosis in a Human Dopaminergic Cell Line The purpose of this experiment was to evaluate the expression of PIG3 and cell viability in an in vitro chemical model of Parkinson's Disease. The in vitro model involved the use of a human dopaminergic cell line, SH-SY5Y, treated with rotenone. Rotenone is known to induce death of dopaminergic neurons in experimental animals, and injection of rotenone into rats was reported to cause the development of symptoms similar to those of Parkinson's Disease (PD) (Betarbet et al., 2000, *Nature Neuroscience* 3:1301; Caboni et al., 2004, *Chem. Res. Toxicol.* 17(11):1540-8). The structure of rotenone is show below:

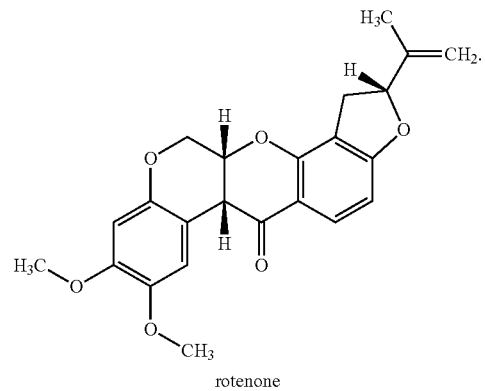 [SMILES: C=C(C)[C@H]1Cc2c(ccc3c2O[C@H]2COc4cc(OC)c(OC)cc4[C@H]2C3=O)O1]

rotenone

For the experiment, SH-SY5Y cells were treated with rotenone at a concentration of 0, 50, 100 and 500 nm for 48 hours. Following the treatment, the amount of PIG3 protein in the cells and the extent of SH-SY5Y cell death were assessed. Cells treated with etoposide, which is known to induce apoptosis, were used as a positive control. Apoptosis in the treated cells was assessed by measuring the amount of cleaved poly(ADP-ribose) polymerase (PARP).

Figure 7:
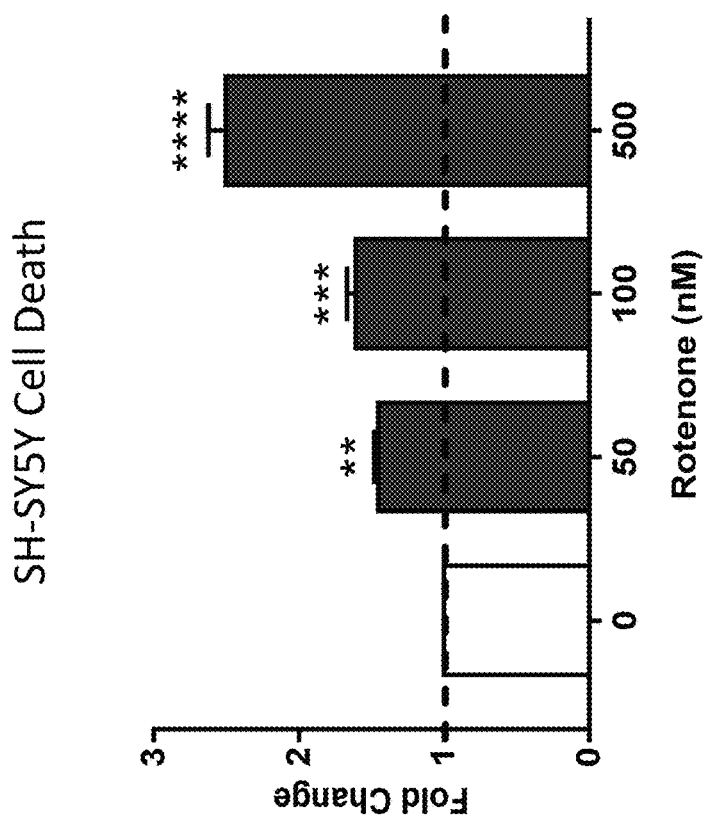
FIG. 7, Panel A is a representative immunoblot showing the amounts of PIG3 and cleaved PARP as a function of rotenone concentration.
Figure 7:
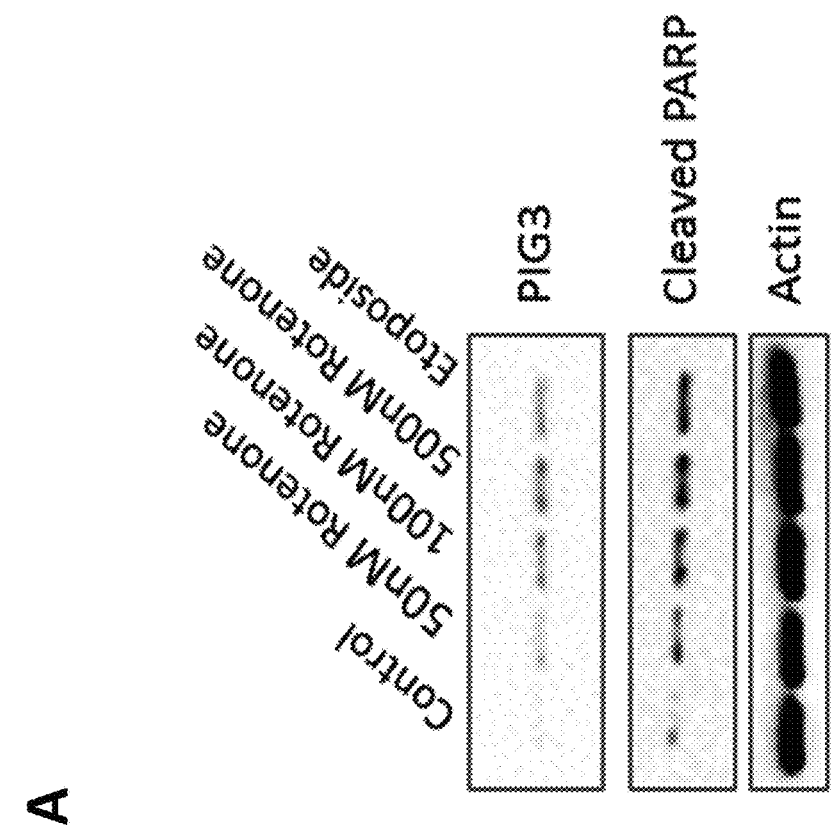

FIG. 7, Panel A is a representative immunoblot showing the amounts of PIG3 and cleaved PARP as a function of rotenone concentration. Actin was used as a loading control. FIG. 7, Panel B is a bar graph showing the relative amount of SH-SY5Y cell death as a function of rotenone concentration. The results demonstrate that the amount of PIG3 protein is increased as a function of increasing concentration of rotenone and that PIG3 expression is associated with rotenone-induced apoptosis in the SH-SY5Y cells.

Example 3: PIG3 Expression is Associated with 6-OHDA-Induced Apoptosis in a Human Dopaminergic Cell Line This experiment was similar to the experiment described in Example 1, except that the in vitro chemical model of Parkinson's Disease involved treatment of SH-SY5Y cells with oxidopamine, also known as 6-hydroxydopamine (6-OHDA) or 2,4,5-trihydroxyphenethylamine 6-OHDA is known to have a selective adverse effect on dopaminergic and noradrenergic neurons. The structure of 6-OHDA is shown below:

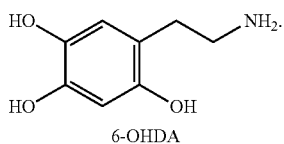 [SMILES: NCCc1cc(O)c(O)cc1O]

6-OHDA

For the experiment, SH-SY5Y cells were treated with 6-OHDA at a concentration of 0, 50 and 100 μm for 48 hours. Following the treatment, the amount of PIG3 protein in the cells and the extent of SH-SY5Y cell death were assessed. Cells treated with etoposide were used as a positive control. Apoptosis in the treated cells was assessed by measuring the amount of cleaved poly(ADP-ribose) polymerase (PARP).

Figure 8:
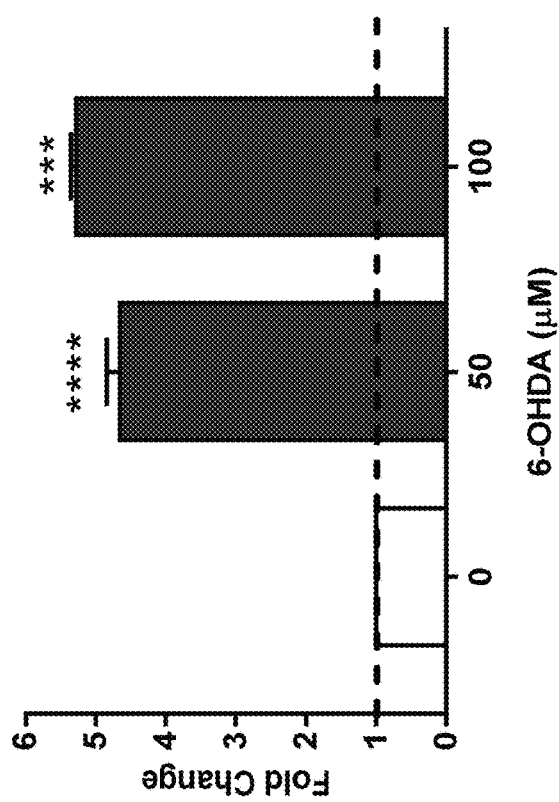
FIG. 8, Panel A is a representative immunoblot showing the amounts of PIG3 and cleaved PARP as a function of 6-OHDA concentration.
Figure 8:
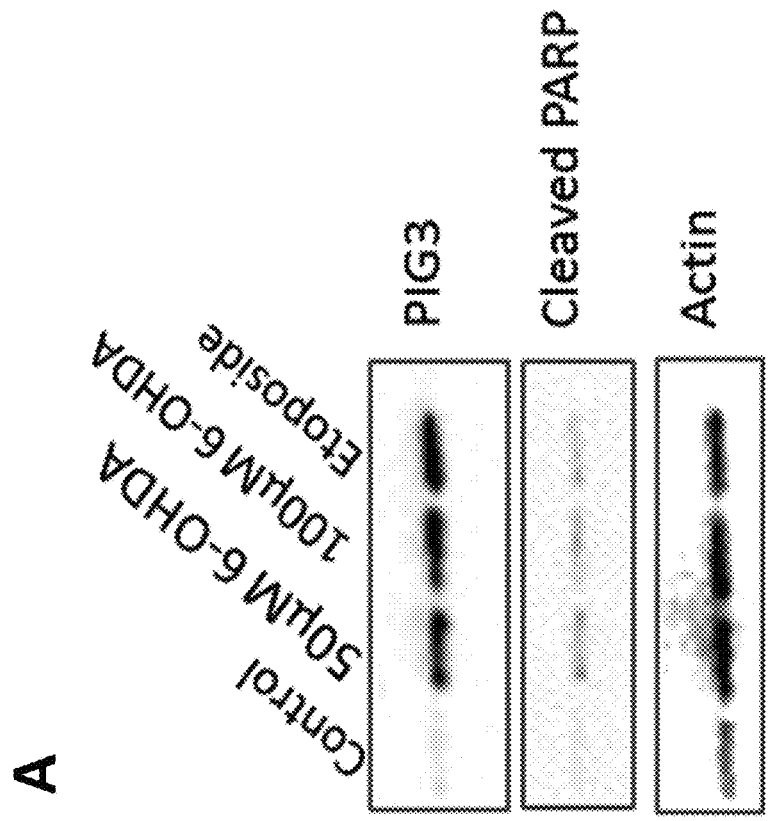

FIG. 8, Panel A is a representative immunoblot showing the amounts of PIG3 and cleaved PARP as a function of 6-OHDA concentration. Actin was used as a loading control. FIG. 8, Panel B is a bar graph showing the relative amount of SH-SY5Y cell death as a function of 6-OHDA concentration. The results demonstrate that the amount of PIG3 protein is increased as a function of increasing concentration of 6-OHDA and that PIG3 expression is associated with 6-OHDA-induced apoptosis in the SH-SY5Y cells.

Example 4: siRNA-Mediated Knockdown of PIG3 is Neuroprotective in Chemical Models of PD The purpose of this experiment was to test the effect of inhibiting the expression of PIG3 in an in vitro chemical model of Parkinson's Disease. For this experiment, an siRNA capable of inhibiting the expression of PIG3 (PIG3 siRNA) was synthesized and tested in SH-SY5Y cells against a non-targeting control mRNA (NTC). Specifically, SH-SY5Y cells were incubated with PIG3 siRNA or NTC for 24 hours followed by rotenone or 6-OHDA for 48 hours at which time cell death and PIG3 expression were measured.

Figure 9:
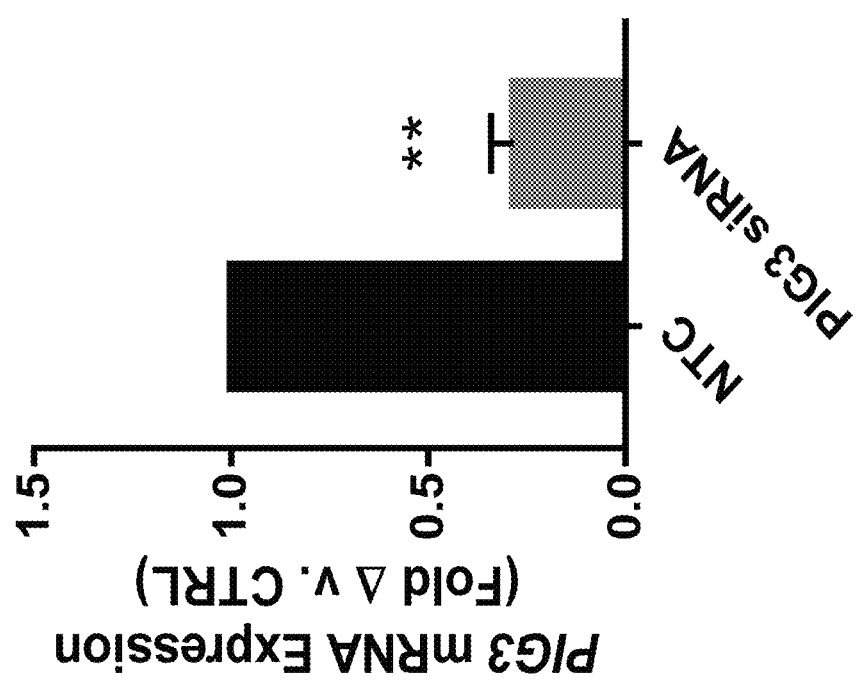
FIG. 9 is a bar graph showing the relative expression of PIG3 mRNA in SH-SY5Y cells treated with a pool of siRNAs directed against PIG3 (PIG3 siRNA) and a non-targeting control siRNA (NTC) at the concentration of 50 nM.
Figure 10:
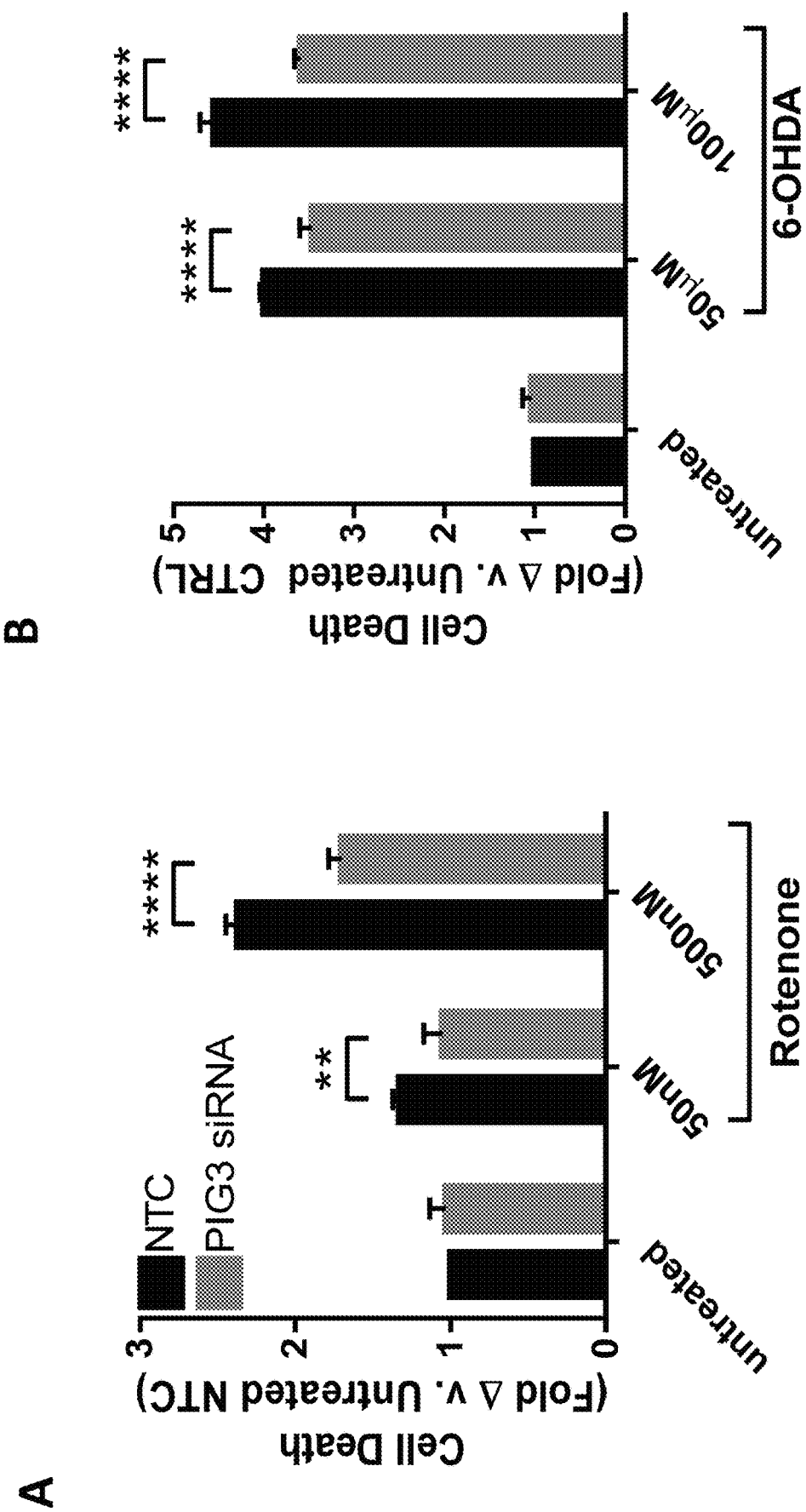
FIG. 10, Panel A is a bar graph showing the relative amount of cell death in SH-SY5Y cells in response to different concentrations of rotenone in the presence of PIG3 siRNA or NTC.

FIG. 9 is a bar graph showing the relative expression of PIG3 mRNA in SH-SY5Y cells treated with a pool of siRNAs directed against PIG3 (PIG3 siRNA) and a non-targeting control siRNA (NTC) at the concentration of 50 nM. The data demonstrates that siRNA is effective in reducing the expression of PIG3 mRNA by more than 2-fold. FIG. 10, Panel A is a bar graph showing the relative amount of cell death in SH-SY5Y cells in response to different concentrations of rotenone in the presence of PIG3 siRNA or NTC. FIG. 10, Panel B is a bar graph showing the relative amount of cell death in SH-SY5Y cells treated with different concentrations of 6-OHDA in the presence of PIG3 siRNA or NTC. Levels of significance were determined with a One way ANOVA:  $p<0.01$, ** $p<0.0001$.

The data presented in FIGS. 9 and 10 demonstrates that inhibition of PIG3 expression by treatment with PIG3 siRNA can reduce the relative amount of cell death in an in vitro chemical model of Parkinson's Disease.

Figure 11:
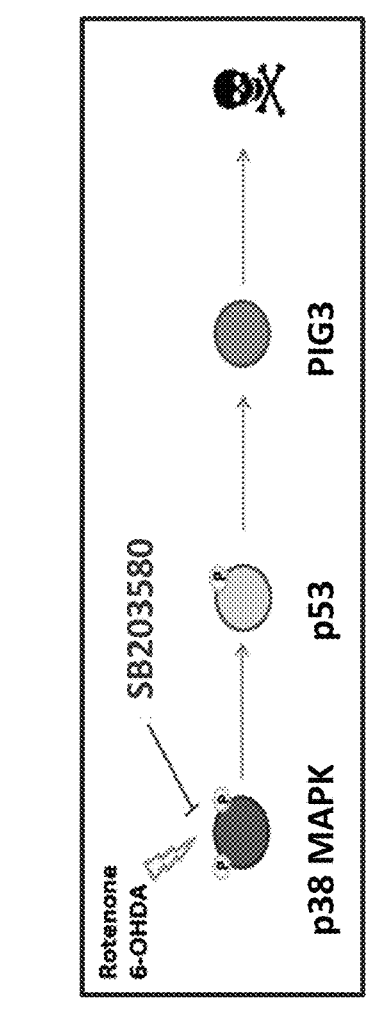
FIG. 11, Panel A is a schematic representation of a portion of a signal transduction cascade in cells treated with rotenone or 6-OHDA.
Figure 11:
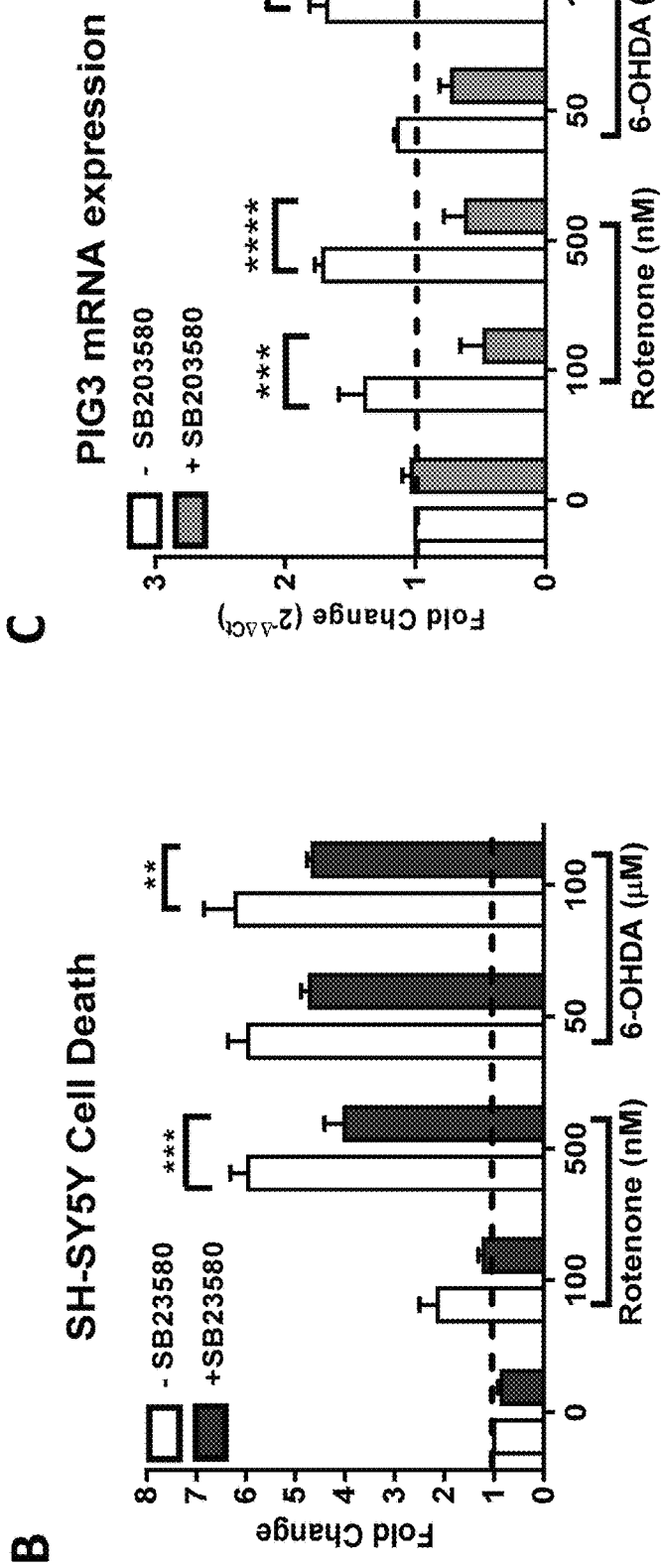

Example 5. Inhibition of MAPK Activity Exerts a Neuroprotective Effect by Reducing PIG3 Transcription As shown in FIG. 11, Panel A, phosphorylation and activation of p38 MAPK as a result of rotenone or 6-OHDA treatment in SH-SY5Y cells leads to phosphorylation and activation of p53, which, in turn, leads to the increased expression of PIG3. The purpose of this experiment was to test the effect of inhibiting the p38 MAPK activity on cell death and the expression of PIG3 in in vitro chemical model of Parkinson's Disease. To this end, SH-SY5Y cells were treated for 48 hours with different concentrations of rotenone or 6-OHDA in the presence of SB203580, a specific inhibitor of p38. SH-SY5Y cell death and PIG3 mRNA expression were assessed following treatment.

FIG. 11, Panel B is a bar graph showing the relative amount of cell death in SH-SY5Y cells treated with rotenone and 6-OHDA in the absence and presence of SB203580. FIG. 11, Panel C is a bar graph showing the relative expression of PIG3 mRNA in SH-SY5Y cells treated with rotenone and 6-OHDA in the absence and presence of SB203580. Levels of significance were determined with a One way ANOVA: * $p<0.05$,  $p<0.01$, * $p<0.005$, **** $p<0.0001$.

The data presented in FIG. 11 indicates that inhibition of p38 MAPK leads to decreased cell death and decreased PIG3 mRNA expression. Thus, inhibition of MAPK activity exerts a neuroprotective effect in an in vitro chemical model of Parkinson's Disease.

Figure 12:
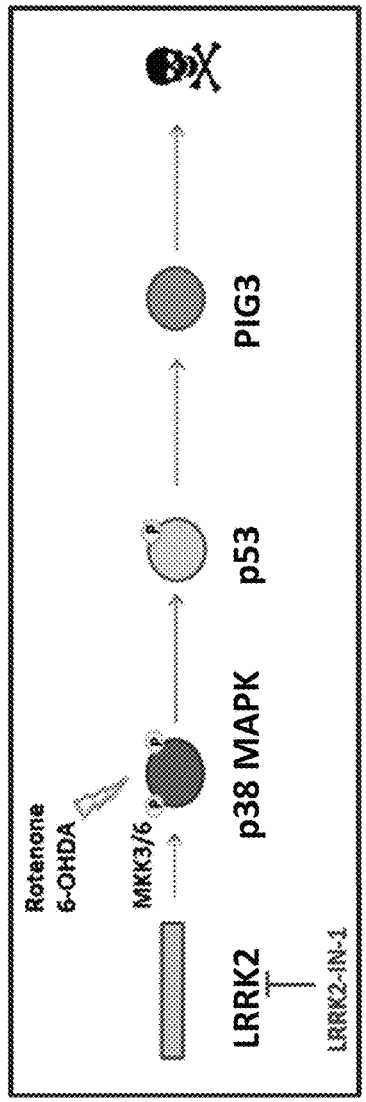
FIG. 12, Panel A is a schematic representation of a portion of a signal transduction cascade in cells treated with rotenone or 6-OHDA.
Figure 12:
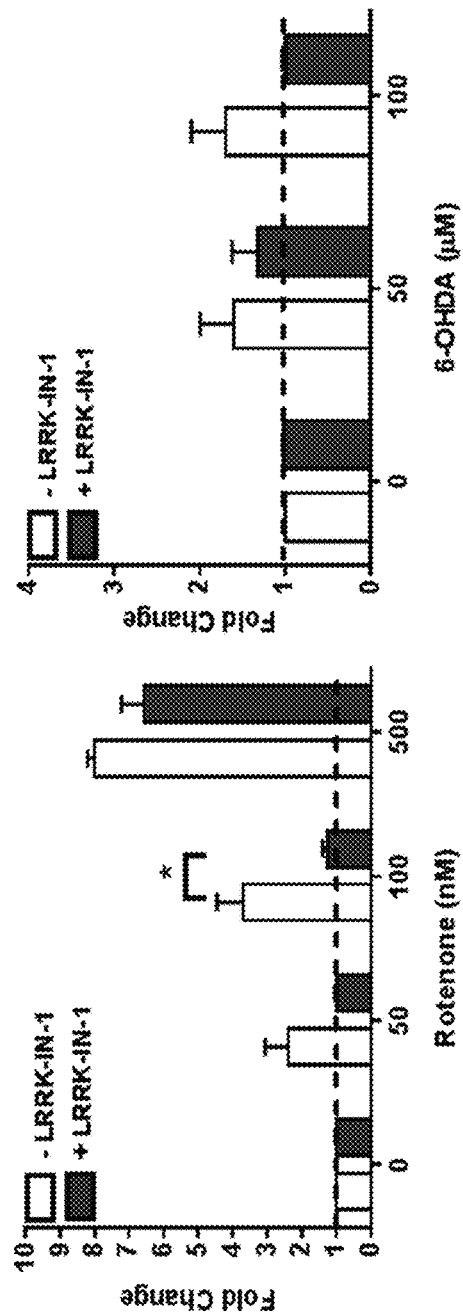

Example 6. Inhibition of LRRK2 Activity Exerts a Neuroprotective Effect by Reducing PIG3 Transcription As shown in FIG. 12, Panel A, leucine-rich repeat kinase 2 (LRRK2), also known as dardarin, acts upstream of the p38 MAPK in the signal transduction cascade resulting from treatment in SH-SY5Y cells with rotenone or 6-OHDA. The purpose of this experiment was to test the effect of inhibiting LRRK2 activity on cell death and the expression of PIG3 in in vitro chemical model of Parkinson's Disease. To this end, SH-SY5Y cells were treated for 48 hours with different concentrations of rotenone or 6-OHDA in the presence of LRRK2-IN-1, a potent and selective inhibitor of LRRK2 kinase activity (as described in, e.g., Deng et al., Nat. Chem. Biol. 2011, 7(4): 203-205, the entire contents of which are incorporated herein by reference). SH-SY5Y cell death and PIG3 mRNA expression were assessed following treatment.

Figure 13:
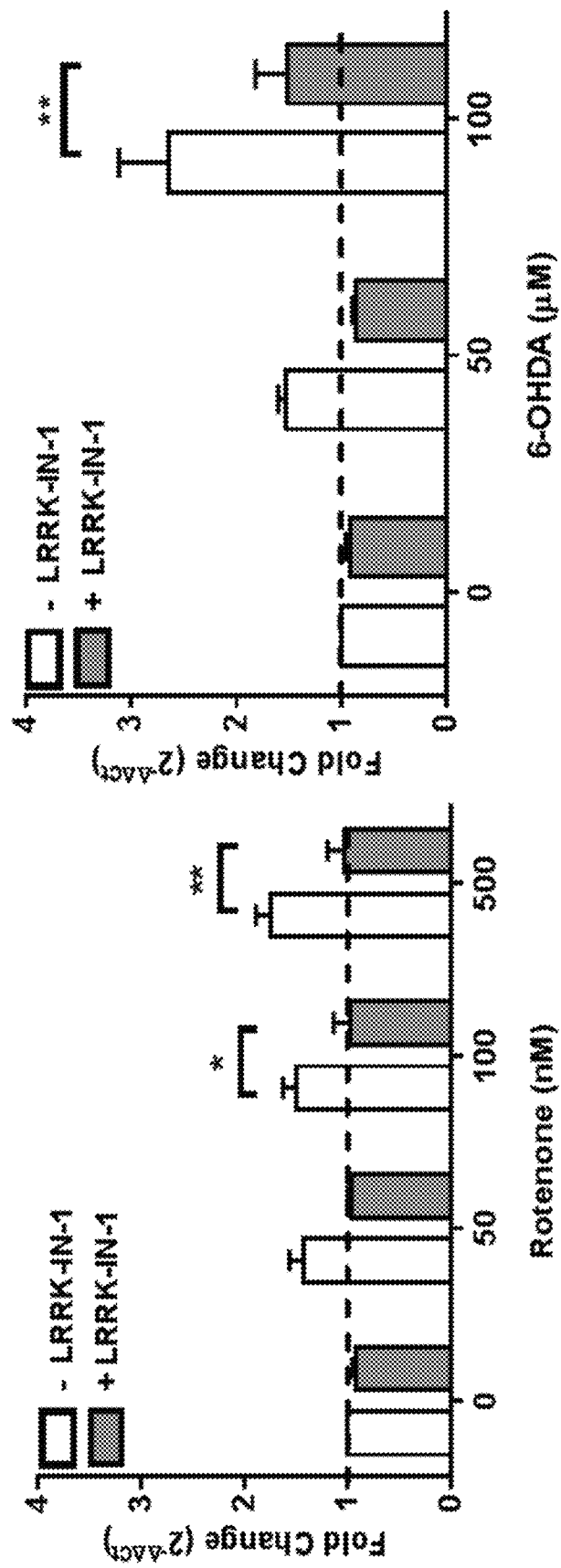
FIG. 13 is a bar graph showing the relative expression of PIG3 mRNA in SH-SY5Y cells treated with rotenone and 6-OHDA in the absence and presence of LRRK2-IN-1.

FIG. 12, Panel B is a bar graph showing the relative amount of cell death in SH-SY5Y cells treated with rotenone and 6-OHDA in the absence and presence of LRRK2-IN-1. FIG. 13 is a bar graph showing the relative expression of PIG3 mRNA in SH-SY5Y cells treated with rotenone and 6-OHDA in the absence and presence of LRRK2-IN-1. Levels of significance were determined with a One way ANOVA: * $p<0.05$, ** $p<0.01$.

The data presented in FIG. 12 indicates that inhibition of LRRK2 leads to decreased cell death and decreased PIG3 mRNA expression. Thus, inhibition of LRRK2 activity exerts a neuroprotective effect in in vitro chemical model of Parkinson's Disease.

Example 7. Overexpression of PIG3 Increases ROS and Reduces Cell Viability

The purpose of this experiment was to access the effect of overexpression of PIG3 on cell viability and reactive oxygen species (ROS) production. To this end, SH-SY5Y cells stably overexpressing the PIG3 open reading frame (PIG3 ORF) were created and characterized by determining their viability, ROS burden and the amount of PIG3 protein produced in response to treatment with 50 nM 6-OHDA. Cell viability was measured relative to the empty vector control, pLOC (CTRL). ROS burden was estimated using DCFDA fluorescence measured by flow cytometry; and the amount of PIG3 protein was measured by immunoblotting and normalizing the densitometry of immunoreactivity to the amount of actin as a loading control.

Figure 14:
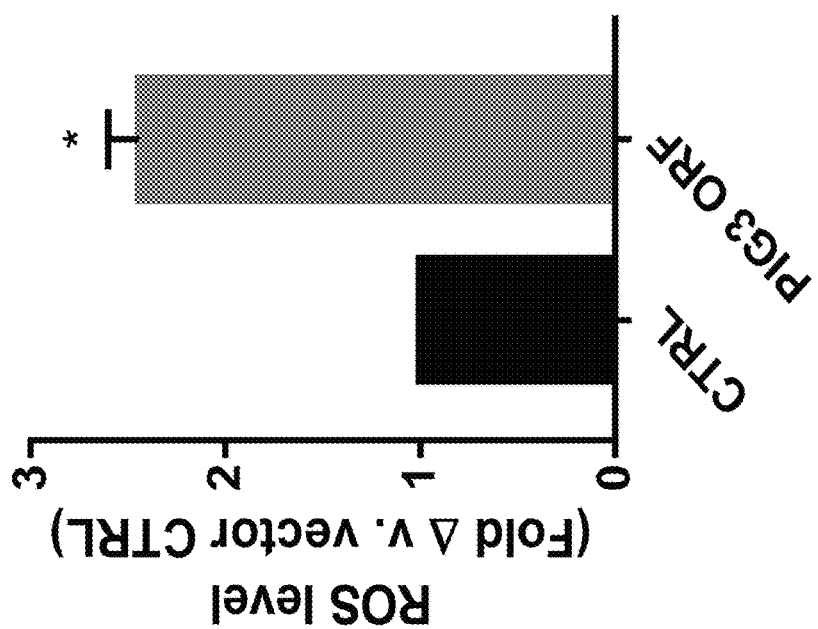
FIG. 14, Panel A is a bar graph showing relative viability of SH-SY5Y cells overexpressing PIG3 ORF as compared to control. The inset shows a representative immunoblot confirming stable PIG3 overexpression in this genetically modified SH-SY5Y model.
Figure 14:
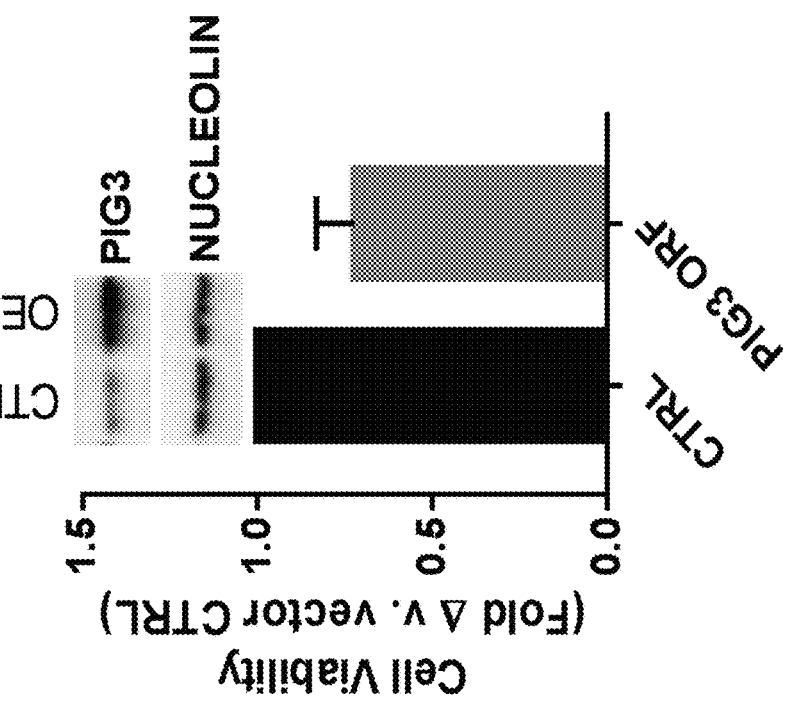

FIG. 14, Panel A is a bar graph showing relative viability of SH-SY5Y cells overexpressing PIG3 ORF as compared to control. The inset shows a representative immunoblot confirming stable PIG3 overexpression in this genetically modified SH-SY5Y model. The data demonstrates that PIG3 overexpression is associated with compromised cell viability. FIG. 14, Panel B is a bar graph showing relative amount of basal ROS in SH-SY5Y cells overexpressing PIG ORF as compared to control. The data demonstrates that PIG3 overexpression is associated with elevated levels of basal ROS.

Figure 15:
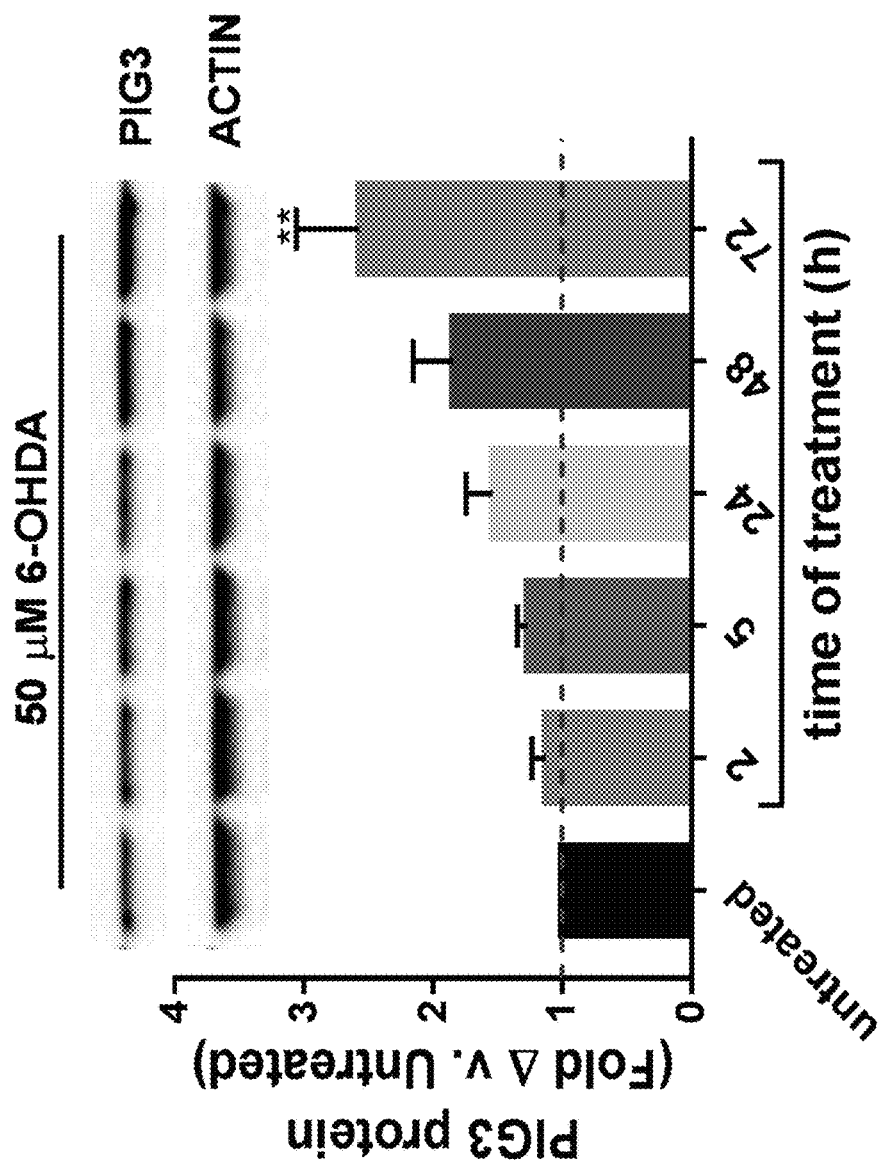
FIG. 15 is a bar graph showing relative amounts of PIG3 protein in SH-Sy5Y cells at different times after treatment with 50 nm 6-OHDA. The inset shows a representative immunoblot of PIG3 protein relative to actin used as a loading control.

FIG. 15 is a bar graph showing relative amounts of PIG3 protein in SH-Sy5Y cells at different times after treatment with 50 nm 6-OHDA. The inset shows a representative immunoblot of PIG3 protein relative to actin used as a loading control. The data in FIG. 15 demonstrates a time-dependent accumulation of PIG3 protein in response to 6-OHDA treatment. Levels of significance were determined with a One way ANOVA: ** $p<0.01$ vs. untreated.

The data presented in FIGS. 14 and 15 demonstrates that overexpression of PIG3 in an in vitro chemical model of Parkinson's Disease leads to increased ROS levels and reduces cell viability.

Example 8. Patient-Specific Induced Pluripotent Stem Cells (iPSCs) Exhibit PIG3 Upregulation Upon Neurotoxin Treatment The purpose of this experiment was to evaluate the expression of PIG3 and cell viability in patient-specific induced pluripotent stem cells (iPSCs) in response to rotenone or 6-OHDA treatment. For the experiment, patient-specific iPSCs were prepared by reprogramming primary dermal fibroblasts harvested from the upper arm of PD+ and unaffected donors using a non-integrating, self-replicating polycistronic RNA construct containing the reprogramming factors OCT4, SOX2, KLF4 and GLIS1 (Millipore, Simplicon™) according to published protocols. The resulting iPSCs were treated with rotenone at a concentration of 0, 10, 50, 100, 500, 750 and 1,000 nm or with 6-OHDA at a concentration of 0.5, 1, 5 and 10 µM. The treatments with rotenone and with 6-OHDA were for 48 hours. Following the treatment, the amount of PIG3 protein in the cells and cell viability were assessed.

Figure 16:
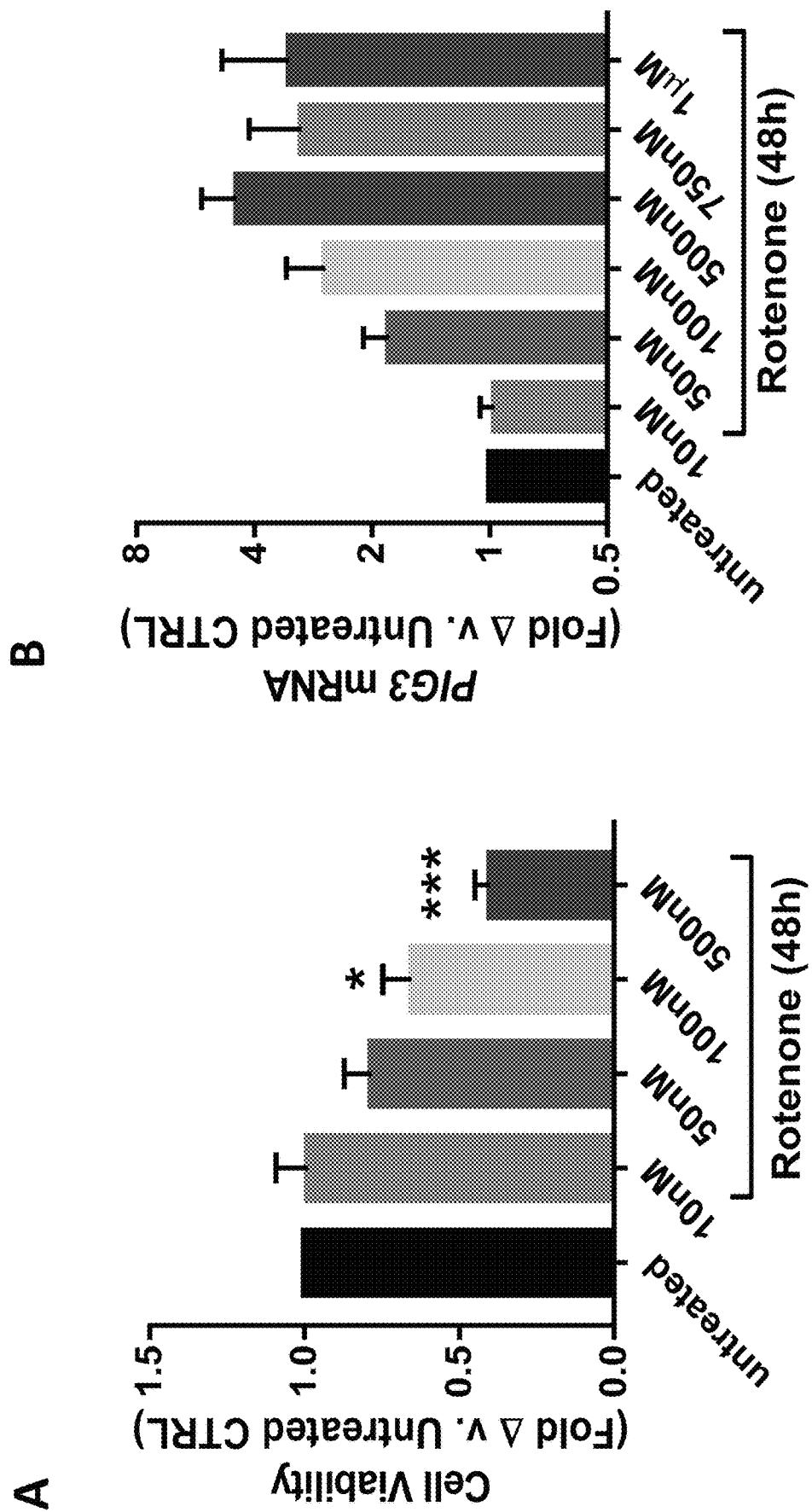
FIG. 16, Panel A is a bar graph showing the relative iPSC viability as a function of rotenone concentration.
Figure 17:
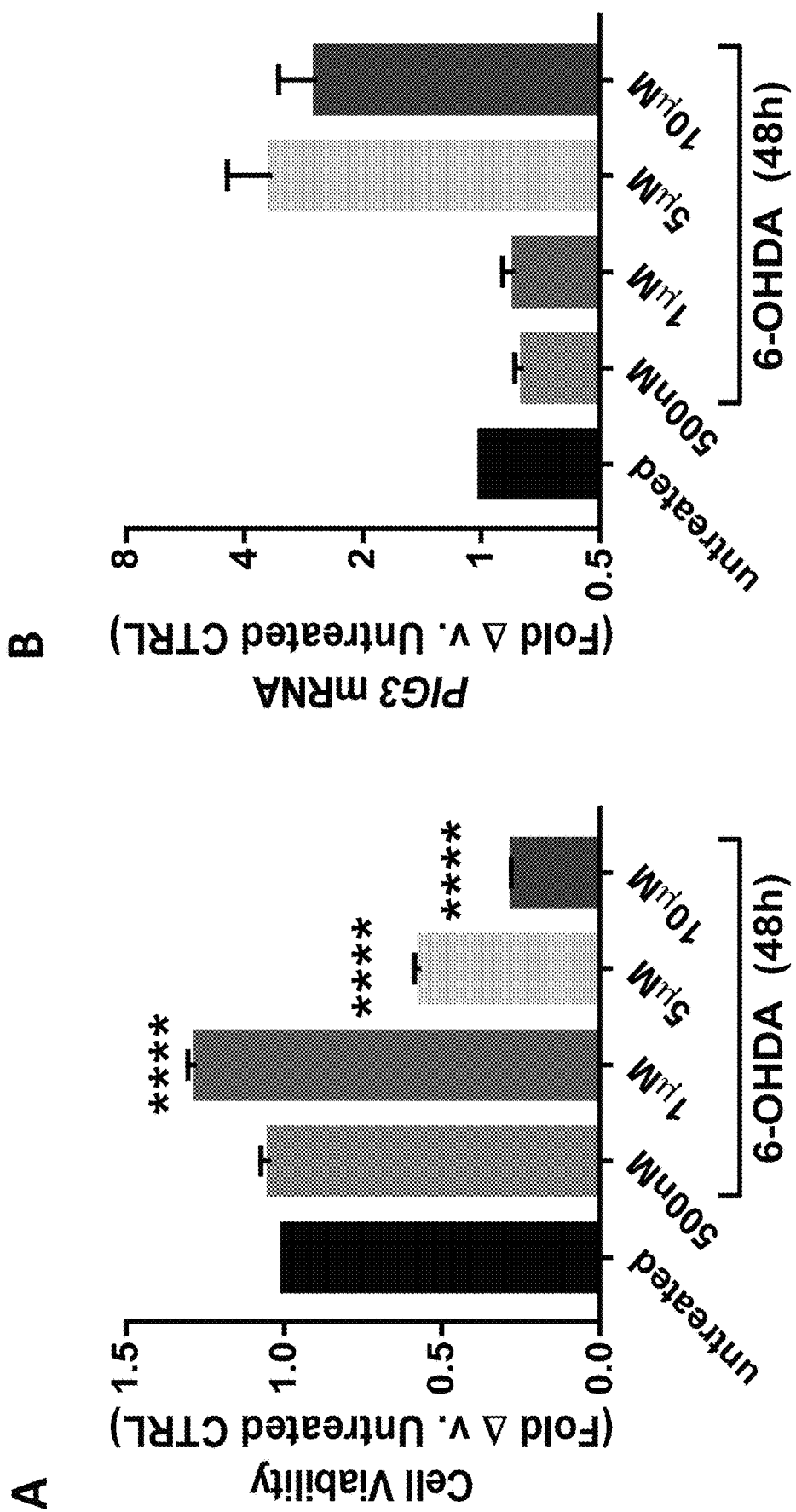
FIG. 17, Panel A is a bar graph showing the relative iPSC viability as a function of 6-OHDA concentration.

FIG. 16, Panel A is a bar graph showing the relative iPSC viability as a function of rotenone concentration. FIG. 16, Panel B is a bar graph showing the relative amount of PIG3 mRNA as a function of rotenone concentration. FIG. 17, Panel A is a bar graph showing the relative iPSC viability as a function of 6-OHDA concentration. FIG. 17, Panel B is a bar graph showing the relative amount of PIG3 mRNA as a function of 6-OHDA concentration. Levels of significance were determined with a one way ANOVA: * $p<0.05$, * $p<0.001$, ** $p<0.0001$ vs. Untreated CTRL (control)

The results presented in FIGS. 16 and 17 demonstrate that patient-specific iPSCs exhibit decreased viability and increased PIG3 expression upon treatment with neurotoxins, rotenone and 6-OHDA.

Example 9. Cells Isolated from Parkinson's Disease Patients Exhibit Chronic MAPK Activation The purpose of this experiment was to assess the status of the MAPK signaling pathway in patients with Parkinson's Disease harboring a G2019S mutation in the LRRK2 gene. The G2019S mutation in LRRK2 gene has been implicated as an important determinant of Parkinson's disease (PD) in both Ashkenazi Jewish and North African Arab populations with carrier frequency of 29.7% among familial and 6% in sporadic Ashkenazi Jewish PD cases. PD patients with the G2019S mutation display similar clinical characteristics to patients with sporadic PD. The G2019S mutation is believed to be responsible for up-regulation of LRRK2 kinase activity, which may ultimately play a role in neuronal loss. See Thaler et al., *J. Neural Transm* (Vienna) 2009, 116(11), 1473-82, the entire contents of which are incorporated herein by reference.

For the experiment, primary fibroblasts were isolated from PD patients with G2019S mutation (LRRK2-PD fibroblasts). Total steady state amount of PIG3 protein was measured in the LRRK2-PD fibroblasts using mass spectrometry. The activity of MKK3 in LRRK2-PD fibroblasts was measured by assessing phosphorylation at Ser218/Thr222 using ELISA using ELISA. The amount of total p53 protein and the levels of p53 phosphorylation at Ser15 in LRRK2-PD fibroblasts were measured by using ELISA. The LRRK2-PD fibroblasts were also used to prepare iPSC-derived neurons (LRRK2-PD). Specifically, primary dermal fibroblasts harvested from the upper arm of PD+ and unaffected donors were reprogrammed using a non-integrating, self-replicating polycistronic RNA construct containing the reprogramming factors OCT4, SOX2, KLF4 and GLIS1 (Millipore, Simplicon™) according to published protocols. Upon successful reprogramming, iPSCs were characterized and subsequently differentiated towards excitatory cortical neurons following published protocols (Shi et al., Nat. Neurosci. 2012, 15(3):10.1038; Chamber et al. *Nat. Biotechnology*, 2009, 27:275-280, the entire contents of which are incorporated herein by reference). The LRRK2-PD neurons were characterized by assessing the total levels of p53 and basal PIG3. Cells from healthy donors were used as controls.

Figure 18:
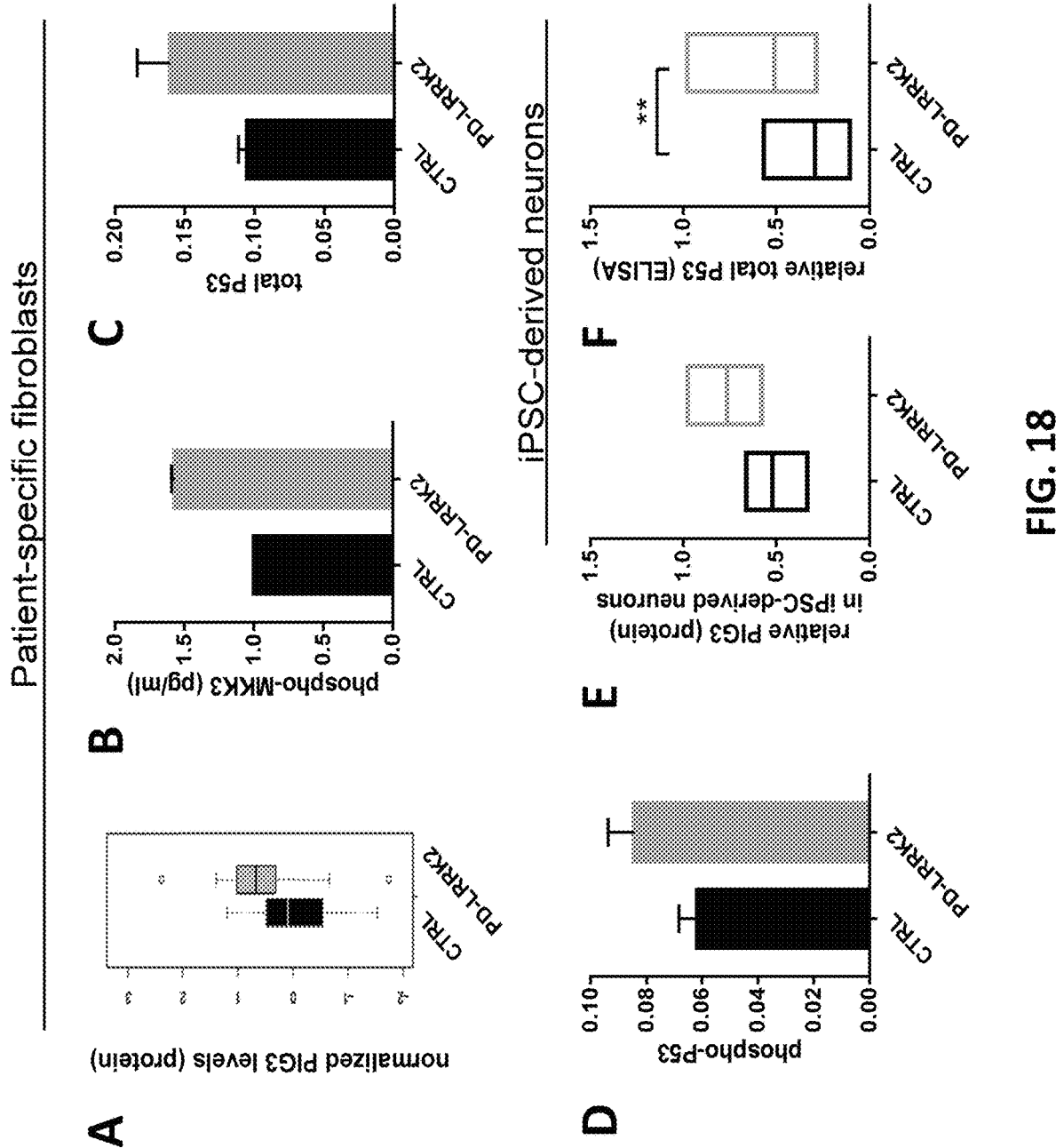
FIG. 18, Panel A is a boxplot showing the steady state amount of PIG3 protein in LRRK2-PD fibroblasts relative to controls.

FIG. 18, Panel A is a boxplot showing the steady state amount of PIG3 protein in LRRK2-PD fibroblasts relative to controls. FIG. 18, Panel B is a bar graph showing the amount of MKK3 phosphorylation in LRRK2-PD fibroblasts and controls. FIG. 18, Panel C is a bar graph showing the total amount of p53 in the LRRK2-PD fibroblasts and controls. FIG. 18, Panel D is a bar graph showing the total amount of p53 phosphorylation in the LRRK2-PD fibroblasts and controls. FIG. 18, Panel E is a boxplot showing the relative amounts of PIG3 protein in the iPSC-derived neurons prepared from the LRRK2-PD fibroblasts and controls. FIG. 18, Panel F is a boxplot showing the relative amounts of p53 protein in the iPSC-derived neurons prepared from the LRRK2-PD fibroblasts and controls. Levels of significance were determined with a one way ANOVA: $p<0.05$,  $p<0.01$, *$p<0.001$ vs. CTRL (control).

The results presented in FIG. 18 indicate the importance of the upregulation of the MAPK pathway in modulating PIG3 transactivation.

Example 10. G2019S Mutation in LRRK2 Gene is Associated with Increased PIG3 in iPSC-Derived Neurons The purpose of this experiment was to evaluate the effect of treatment with neurotoxins, such as rotenone and 6-OHDA in iPSC-derived neurons that were prepared from LRRK2-PD fibroblasts (LRRK2-PD neurons). IPSCs were prepared from LRRK2-PD fibroblasts and then differentiated towards excitatory cortical neurons as described in the above examples and following published protocols (e.g., Shi et al., Nat. Neurosci. 2012, 15(3):10.1038; Chamber et al. Nat. Biotechnology, 2009, 27:275-280, the entire contents of which are incorporated herein by reference). Subsequently, LRRK2-PD neurons were then treated with increasing concentrations of rotenone and 6-OHDA, and relative amounts of PIG3 protein and cleaved PARP protein were measured. iPSC-derived neurons prepared from cells isolated from healthy donors were used as controls.

Figure 19:
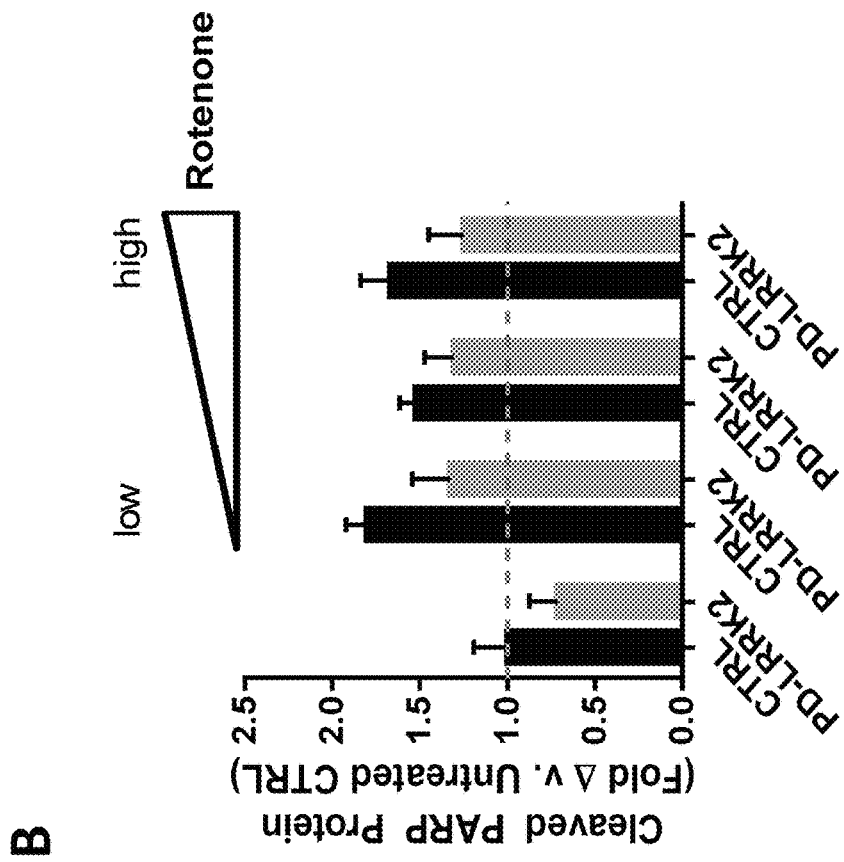
FIG. 19, Panel A is a bar graph showing the amount of PIG3 protein in LRRK2-PD neurons and controls as a function of increasing concentrations of rotenone.
Figure 19:
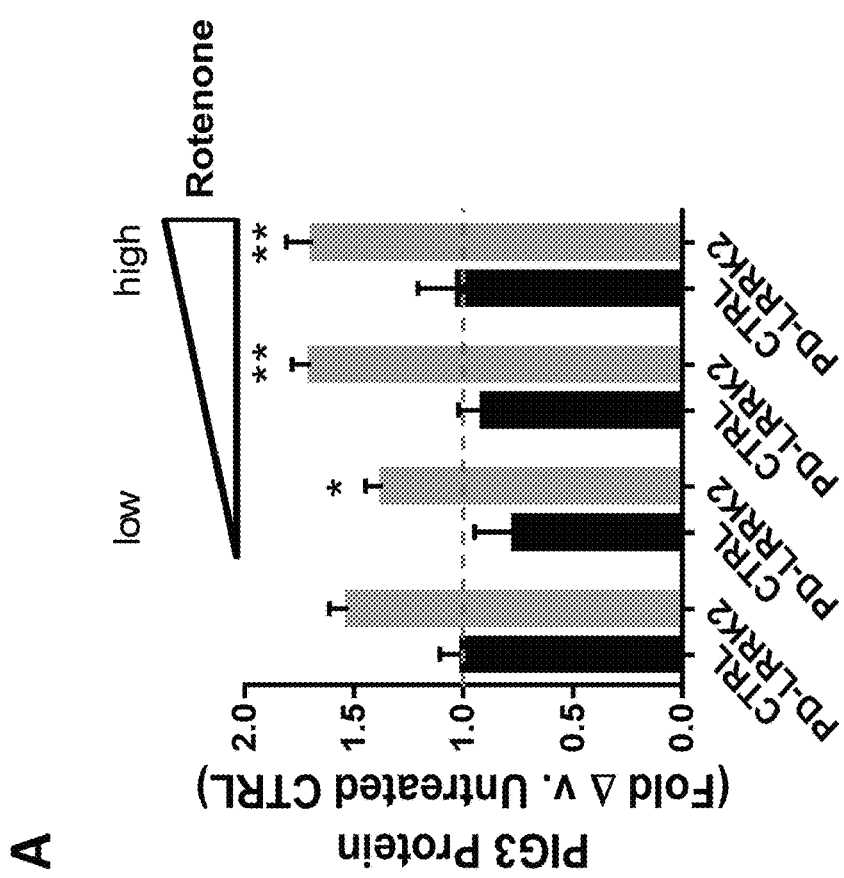
Figure 20:
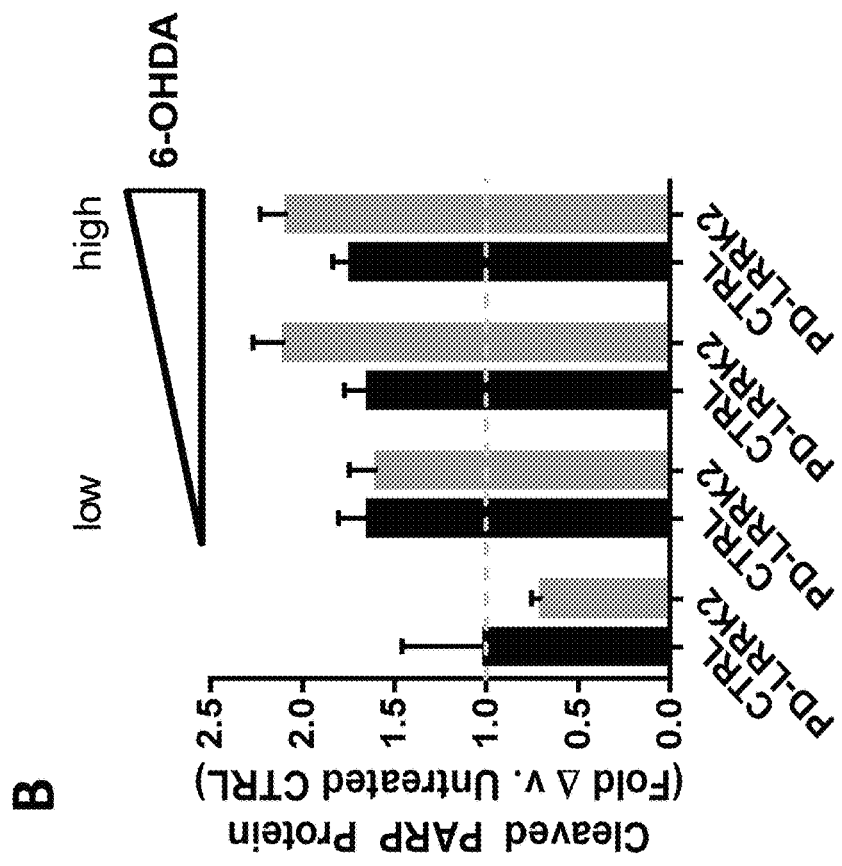
FIG. 20, Panel A is a bar graph showing the amount of PIG3 protein in LRRK2-PD neurons and controls as a function of increasing concentrations of 6-OHDA.
Figure 20:
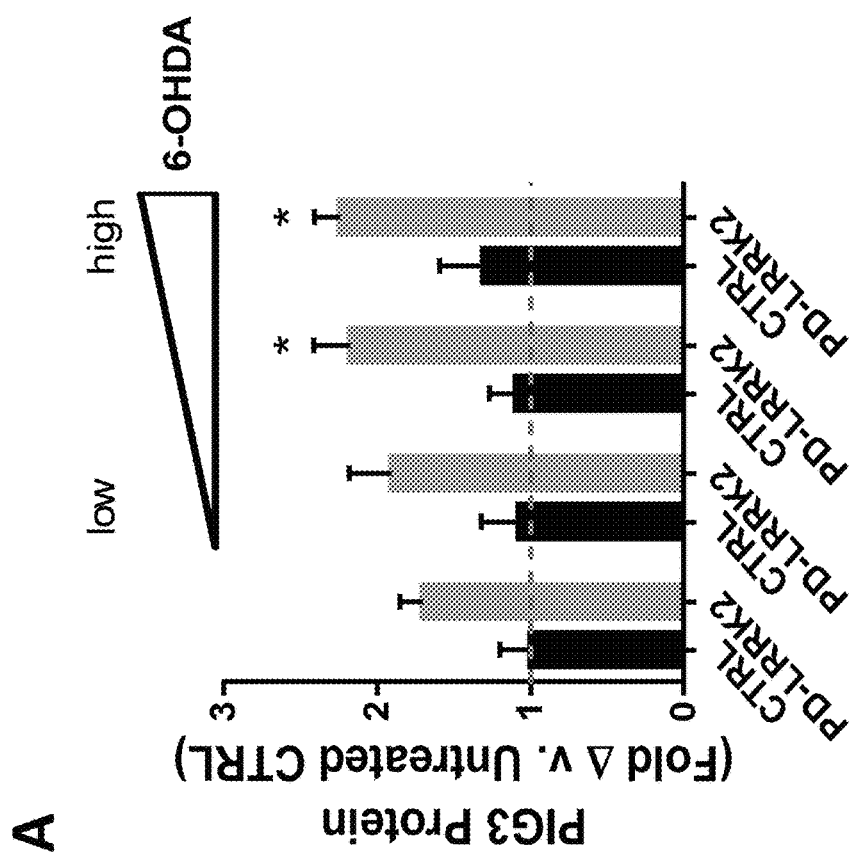

FIG. 19, Panel A is a bar graph showing the amount of PIG3 protein in LRRK2-PD neurons and controls as a function of increasing concentrations of rotenone. FIG. 19, Panel B is a bar graph showing the amount of cleaved PARP protein LRRK2-PD neurons and controls as a function of increasing concentrations of rotenone. FIG. 20, Panel A is a bar graph showing the amount of PIG3 protein in LRRK2-PD neurons and controls as a function of increasing concentrations of 6-OHDA. FIG. 20, Panel B is a bar graph showing the amount of cleaved PARP protein in LRRK2-PD neurons and controls as a function of increasing concentrations of 6-OHDA. Levels of significance were determined with a one way ANOVA: * $p<0.05$, ** $p<0.01$, vs. Untreated CTRL (control) of same concentration of neurotoxin.

The results presented in FIGS. 19 and 20 indicate that, compared to neurons derived from healthy controls, LRRK2-PD neurons exhibit increased basal levels of PIG 3 protein expression in the absence of significant changes in apoptotic markers, such as cleaved PARP. Induction of stress results in further increases in PIG3 protein and cleaved PARP expression.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

INFORMAL SEQUENCE LISTING

SEQ ID NO: 1
>AAC39528.1 Pig3 [Homo sapiens]
MLAVHFDKPGGPENLYVKEVAKPSPGEGEVLLKVAASALNRADLMQRQGQ
YDPPPGASNILGLEASGHVAELGPGCQGHWKIGDTAMALLPGGGQAQYVT
VPEGLLMPIPEGLTLTQAAAIPEAWLTAFQLLHLVGNVQAGDYVLIHAGL
SGVGTAAIQLTRMAGAIPLVTAGSQKKLQMAEKLGAAAGFNYKKEDFSEA
TLKFTKGAGVNLILDCIGGSYWEKNVNCLALDGRWVLYGLMGGGDINGPL
FSKLLFKRGSLITSLLRSRDNKYKQMLVNAFTEQILPHFSTEGPQRLLPV
LDRIYPVTEIQEAHSTWRPTRT SEQ ID NO: 2
>AID60277.1 glucosylceramidase [Homo sapiens]
MEFSSPSREECPKPLSRVSIMAGSLTGLLLLQAVSWASGARPCIPKSFGY
SSVVCVCNATYCDSFDPPTFPALGTFSRYESTRSGRRMELSMGPIQANHT
GTGLLLTLQPEQKFQKVKGFGGAMTDAAALNILALSPPAQNLLLKSYFSE
EGIGYNIIRVPMASCDFSIRTYTYADTPDDFQLHNFSLPEEDTKLKIPLI
HRALQLAQRPVSLLASPWTSPTWLKTNGAVNGKGSLKGQPGDIYHQTWAR
YFVKFLDAYAEHKLQFWAVTAENEPSAGLLSGYPFQCLGFTPEHQRDFIA
RDLGPTLANSTHHNVRLLMLDDQRLLLPHWAKVVLTDPEAAKYVHGIAVH
WYLDFLAPAKATLGETHRLFPNTMLFASEACVGSKFWEQSVRLGSWDRGM
QYSHSIITNLLYHVVGWTDWNLALNPEGGPNWVRNFVDSPIIVDITKDTF
YKQPMFYHLGHFSKFIPEGSQRVGLVASQKNDLDAVALMHPDGSAVVVVL
NRSSKDVPLTIKDPAVGFLETISPGYSIHTYLWRRQ SEQ ID NO: 3
>NP_003349.1 ceramide glucosyltransferase [Homo sapiens]
MALLDLALEGMAVFGFVLFLVLWLMHFMAIIYTRLHLNKKATDKQPYSKL
PGVSLLKPLKGVDPNLINNLETFFELDYPKYEVLLCVQDHDDPAIDVCKK
LLGKYPNVDARLFIGGKKVGINPKINNLMPGYEVAKYDLIWICDSGIRVI
PDTLTDMVNQMTEKVGLVHGLPYVADRQGFAATLEQVYFGTSHPRYYISA
NVTGFKCVTGMSCLMRKDVLDQAGGLIAFAQYIAEDYFMAKAIADRGWRF
AMSTQVAMQNSGSYSISQFQSRMIRWTKLRINMLPATIICEPISECFVAS
LIIGWAAHHVFRWDIMVFFMCHCLAWFIFDYIQLRGVQGGTLCFSKLDYA
VAWFIRESMTIYIFLSALWDPTISWRTGRYRLRCGGTAEEILDV SEQ ID NO: 4
>NP_940980.3 leucine-rich repeat serine/threonine-protein kinase 2 [Homo sapiens]
MASGSCQGCEEDEETLKKLIVRLNNVQEGKQIETLVQILEDLLVFTYSEH
ASKLFQGKNIHVPLLIVLDSYMRVASVQQVGWSLLCKLIEVCPGTMQSLM
GPQDVGNDWEVLGVHQLILKMLTVHNASVNLSVIGLKTLDLLLTSGKITL
LILDEESDIFMLIFDAMHSFPANDEVQKLGCKALHVLFERVSEEQLTEFV
ENKDYMILLSALTNFKDEEEIVLHVLHCLHSLAIPCNNVEVLMSGNVRCY
NIVVEAMKAFPMSERIQEVSCCLLHRLTLGNFFNILVLNEVHEFVVKAVQ
QYPENAALQISALSCLALLTETIFLNQDLEEKNENQENDDEGEEDKLFWL
EACYKALTWHRKNKHVQEAACWALNNLLMYQNSLHEKIGDEDGHFPAHRE
VMLSMLMHSSSKEVFQASANALSTLLEQNVNFRKILLSKGIHLNVLELMQ
KHIHSPEVAESGCKMLNHLFEGSNTSLDIMAAVVPKILTVMKRHETSLPV
QLEALRAILHFIVPGMPEESREDTEFHHKLNMVKKQCFKNDIHKLVLAAL
NRFIGNPGIQKCGLKVISSIVHFPDALEMLSLEGAMDSVLHTLQMYPDDQ
EIQCLGLSLIGYLITKKNVFIGTGHLLAKILVSSLYRFKDVAEIQTKGFQ
TILAILKLSASFSKLLVHHSFDLVIFHQMSSNIMEQKDQQFLNLCCKCFA
KVAMDDYLKNVMLERACDQNNSIMVECLLLLGADANQAKEGSSLICQVCE
KESSPKLVELLLNSGSREQDVRKALTISIGKGDSQIISLLLRRLALDVAN
NSICLGGFCIGKVEPSWLGPLFPDKTSNLRKQTNIASTLARMVIRYQMKS
AVEEGTASGSDGNFSEDVLSKFDEWTFIPDSSMDSVFAQSDDLDSEGSEG
SFLVKKKSNSISVGEFYRDAVLQRCSPNLQRHSNSLGPIFDHEDLLKRKR
KILSSDDSLRSSKLQSHMRHSDSISSLASEREYITSLDLSANELRDIDAL
SQKCCISVHLEHLEKLELHQNALTSFPQQLCETLKSLTHLDLHSNKFTSF
PSYLLKMSCIANLDVSRNDIGPSVVLDPTVKCPTLKQFNLSYNQLSFVPE
NLTDVVEKLEQLILEGNKISGICSPLRLKELKILNLSKNHISSLSENFLE
ACPKVESFSARMNFLAAMPFLPPSMTILKLSQNKFSCIPEAILNLPHLRS
LDMSSNDIQYLPGPAHWKSLNLRELLFSHNQISILDLSEKAYLWSRVEKL
HLSHNKLKEIPPEIGCLENLTSLDVSYNLELRSFPNEMGKLSKIWDLPLD
ELHLNFDFKHIGCKAKDIIRFLQQRLKKAVPYNRMKLMIVGNTGSGKTTL
LQQLMKTKKSDLGMQSATVGIDVKDWPIQIRDKRKRDLVLNVWDFAGREE
FYSTHPHFMTQRALYLAVYDLSKGQAEVDAMKPWLFNIKARASSSPVILV
GTHLDVSDEKQRKACMSKITKELLNKRGFPAIRDYHFVNATEESDALAKL
RKTIINESLNFKIRDQLVVGQLIPDCYVELEKIILSERKNVPIEFPVIDR
KRLLQLVRENQLQLDENELPHAVHFLNESGVLLHFQDPALQLSDLYFVEP
KWLCKIMAQILTVKVEGCPKHPKGIISRRDVEKFLSKKRKFPKNYMSQYF
KLLEKFQIALPIGEEYLLVPSSLSDHRPVIELPHCENSEIIIRLYEMPYF
PMGFWSRLINRLLEISPYMLSGRERALRPNRMYWRQGIYLNWSPEAYCLG
SEVLDNHPESFLKITVPSCRKGCILLGQVVDHIDSLMEEWFPGLLEIDIC
GEGETLLKKWALYSFNDGEEHQKILLDDLMKKAEEGDLLVNPDQPRLTIP
ISQIAPDLILADLPRNIMLNNDELEFEQAPEFLLGDGSFGSVYRAAYEGE
EVAVKIFNKHTSLRLLRQELVVLCHLHHPSLISLLAAGIRPRMLVMELAS
KGSLDRLLQQDKASLTRTLQHRIALHVADGLRYLHSAMIIYRDLKPHNVL
LFTLYPNAAIIAKIADYGIAQYCCRMGIKTSEGTPGFRAPEVARGNVIYN
QQADVYSFGLLLYDILTTGGRIVEGLKFPNEFDELEIQGKLPDPVKEYGC

INFORMAL SEQUENCE LISTING

APWPMVEKLIKQCLKENPQERPTSAQVFDILNSAELVCLTRRILLPKNVI
VECMVATHHNSRNASIWLGCGHTDRGQLSFLDLNTEGYTSEEVADSRILC
LALVHLPVEKESWIVSGTQSGTLLVINTEDGKKRHTLEKMTDSVTCLYCN
SFSKQSKQKNFLLVGTADGKLAIFEDKTVKLKGAAPLKILNIGNVSTPLM
CLSESTNSTERNVMWGGCGTKIFSFSNDFTIQKLIETRTSQLFSYAAFSD
SNIITVVVDTALYIAKQNSPVVEVWDKKTEKLCGLIDCVHFLREVMVKEN
KESKHKMSYSGRVKTLCLQKNTALWIGTGGGHILLLDLSTRRLIRVIYNF
CNSVRVMMTAQLGSLKNVMLVLGYNRKNTEGTQKQKEIQSCLTVWDINLP
HEVQNLEKHIEVRKELAEKMRRTSVE

INFORMAL SEQUENCE LISTING

SEQ ID NO: 5
5'-CCGGATGGCTGGAGCTATT-3'

SEQ ID NO: 6
5'-TGTTCAGGCTGGAGACTAT-3'

SEQ ID NO: 7
5'-AAAUGUUCAGGCUGGAGACUA-3'

What is claimed is:

1. A method of treating Parkinson's Disease (PD) in a human subject in need thereof, the method comprising administering to the subject an inhibitor of human p53-inducible gene 3 (PIG3) (PIG3 inhibitor), wherein the inhibitor inhibits PIG3 by associating with or binding PIG3 mRNA, wherein the inhibitor comprises a nucleic acid selected from the group consisting of an antisense nucleic acid molecule, an siRNA, an shRNA, and a dicer substrate siRNA (DsiRNA), and wherein the subject has an increased expression level of PIG3, thereby treating the Parkinson's disease in the subject.

2. The method of claim 1, wherein the PD is an idiopathic PD.

3. The method of claim 2, wherein the PD is associated with a genetic mutation.

4. The method of claim 3, wherein the genetic mutation is in the glucocerebrosidase (GBA) gene.

5. The method of claim 4, further comprising the step of:
identifying the subject as having a genetic mutation in the GBA gene.

6. The method of claim 4, wherein the genetic mutation in the GBA gene is selected from the group consisting of N370S mutation and L444P mutation.

7. The method of claim 3, wherein the genetic mutation is in the leucine rich repeat kinase 2 (LRRK2) gene.

8. The method of claim 7, further comprising the step of:
identifying the subject as having a genetic mutation in the LRRK2 gene.

9. The method of claim 8, wherein the genetic mutation in the LRRK2 gene is selected from the group consisting of G2019S mutation, R1441C mutation, R1441G mutation, R1441H mutation, Y1699C mutation, I2020T mutation and N1437H mutation.

10. The method of claim 9, wherein the genetic mutation in the LRRK2 gene is the G2019S mutation.

11. The method of claim 1, wherein administering the PIG3 inhibitor to the subject results in inhibition or in slowing down of PD progression in the subject as measured by UPDRS.

12. A method of reducing neuronal cell death in a human subject afflicted with Parkinson's Disease (PD), comprising administering to the subject an inhibitor of p53-inducible gene 3 (PIG3) (PIG3 inhibitor), wherein the inhibitor inhibits PIG3 by associating with or binding to PIG3 mRNA, wherein the inhibitor comprises a nucleic acid selected from the group consisting of an antisense nucleic acid molecule, an siRNA, an shRNA, and a dicer substrate siRNA (DsiRNA), and wherein the subject has an increased expression level of PIG3, thereby treating the Parkinson's disease in the subject.

13. The method of claim 12, wherein the neuronal death is glucocerebrosidase (GCase)-mediated neuronal cell death and wherein the Parkinson's disease is associated with a genetic mutation in the glucocerebrosidase (GBA) gene.

14. The method of claim 13, wherein the genetic mutation in the GBA gene is selected from the group consisting of N370S mutation and L444P mutation.

15. A method of treating Parkinson's Disease (PD) in a human subject in need thereof, wherein the Parkinson's Disease is associated with a genetic mutation in the glucocerebrosidase (GBA) gene, the method comprising administering to the subject an inhibitor of human p53-inducible gene 3 (PIG3) (PIG3 inhibitor) in combination with an inhibitor of human glucosylceramide synthase (GCS inhibitor),
- wherein the PIG3 inhibitor inhibits PIG3 by associating with or binding to PIG3 mRNA, wherein the inhibitor comprises a nucleic acid selected from the group consisting of an antisense nucleic acid molecule, an siRNA, an shRNA, and a dicer substrate siRNA (DsiRNA),
- wherein the GCS inhibitor is selected from the group consisting of GZ/SAR402671 and GZ667161, and wherein the subject has an elevated expression level of PIG3, thereby treating the Parkinson's disease in the subject.

16. The method of claim 15, wherein administering the PIG3 inhibitor to the subject results in inhibition or in slowing down of PD progression in the subject as measured by UPDRS.

\* \* \* \* \*

SEQUENCE LISTING

<160> NUMBER OF SEQ ID NOS: 7

<210> SEQ ID NO 1
<211> LENGTH: 322
<212> TYPE: PRT
<213> ORGANISM: Homo sapiens
<220> FEATURE:
<221> NAME/KEY: misc_feature
<223> OTHER INFORMATION: Pig3

<400> SEQUENCE: 1

Met Leu Ala Val His Phe Asp Lys Pro Gly Gly Pro Glu Asn Leu Tyr
1               5                   10                  15

Val Lys Glu Val Ala Lys Pro Ser Pro Gly Glu Gly Val Leu Leu
            20                  25                  30

Lys Val Ala Ala Ser Ala Leu Asn Arg Ala Asp Leu Met Gln Arg Gln
            35                  40                  45

Gly Gln Tyr Asp Pro Pro Pro Gly Ala Ser Asn Ile Leu Gly Leu Glu
        50                  55                  60

Ala Ser Gly His Val Ala Glu Leu Gly Pro Gly Cys Gln Gly His Trp
65                  70                  75                  80

Lys Ile Gly Asp Thr Ala Met Ala Leu Leu Pro Gly Gly Gly Gln Ala
                85                  90                  95

Gln Tyr Val Thr Val Pro Glu Gly Leu Leu Met Pro Ile Pro Glu Gly
            100                 105                 110

Leu Thr Leu Thr Gln Ala Ala Ala Ile Pro Glu Ala Trp Leu Thr Ala
            115                 120                 125

Phe Gln Leu Leu His Leu Val Gly Asn Val Gln Ala Gly Asp Tyr Val
        130                 135                 140

Leu Ile His Ala Gly Leu Ser Gly Val Gly Thr Ala Ala Ile Gln Leu
145                 150                 155                 160

Thr Arg Met Ala Gly Ala Ile Pro Leu Val Thr Ala Gly Ser Gln Lys
                165                 170                 175

Lys Leu Gln Met Ala Glu Lys Leu Gly Ala Ala Ala Gly Phe Asn Tyr
            180                 185                 190

Lys Lys Glu Asp Phe Ser Glu Ala Thr Leu Lys Phe Thr Lys Gly Ala
            195                 200                 205

Gly Val Asn Leu Ile Leu Asp Cys Ile Gly Gly Ser Tyr Trp Glu Lys
        210                 215                 220

Asn Val Asn Cys Leu Ala Leu Asp Gly Arg Trp Val Leu Tyr Gly Leu
225                 230                 235                 240

Met Gly Gly Gly Asp Ile Asn Gly Pro Leu Phe Ser Lys Leu Leu Phe
                245                 250                 255

Lys Arg Gly Ser Leu Ile Thr Ser Leu Leu Arg Ser Arg Asp Asn Lys

```
                      260                 265                 270
Tyr Lys Gln Met Leu Val Asn Ala Phe Thr Glu Gln Ile Leu Pro His
            275                 280                 285

Phe Ser Thr Glu Gly Pro Gln Arg Leu Leu Pro Val Leu Asp Arg Ile
    290                 295                 300

Tyr Pro Val Thr Glu Ile Gln Glu Ala His Ser Thr Trp Arg Pro Thr
305                 310                 315                 320

Arg Thr

<210> SEQ ID NO 2
<211> LENGTH: 536
<212> TYPE: PRT
<213> ORGANISM: Homo sapiens
<220> FEATURE:
<221> NAME/KEY: misc_feature
<223> OTHER INFORMATION: glucosylceramidase

<400> SEQUENCE: 2

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
            85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
            165                 170                 175

Thr Pro Asp Asp Phe Gln Leu His Asn Phe Ser Leu Pro Glu Glu Asp
        180                 185                 190

Thr Lys Leu Lys Ile Pro Leu Ile His Arg Ala Leu Gln Leu Ala Gln
    195                 200                 205

Arg Pro Val Ser Leu Leu Ala Ser Pro Trp Thr Ser Pro Thr Trp Leu
210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
            245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
```

```
          290                 295                 300
Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
            530                 535

<210> SEQ ID NO 3
<211> LENGTH: 394
<212> TYPE: PRT
<213> ORGANISM: Homo sapiens
<220> FEATURE:
<221> NAME/KEY: misc_feature
<223> OTHER INFORMATION: ceramide glucosyltransferase

<400> SEQUENCE: 3

Met Ala Leu Leu Asp Leu Ala Leu Glu Gly Met Ala Val Phe Gly Phe
1               5                   10                  15

Val Leu Phe Leu Val Leu Trp Leu Met His Phe Met Ala Ile Ile Tyr
            20                  25                  30

Thr Arg Leu His Leu Asn Lys Lys Ala Thr Asp Lys Gln Pro Tyr Ser
        35                  40                  45

Lys Leu Pro Gly Val Ser Leu Leu Pro Leu Lys Gly Val Asp Pro
    50                  55                  60

Asn Leu Ile Asn Asn Leu Glu Thr Phe Phe Glu Leu Asp Tyr Pro Lys
65                  70                  75                  80

Tyr Glu Val Leu Leu Cys Val Gln Asp His Asp Pro Ala Ile Asp
                85                  90                  95

Val Cys Lys Lys Leu Leu Gly Lys Tyr Pro Asn Val Asp Ala Arg Leu
                100                 105                 110
```

-continued

```
Phe Ile Gly Gly Lys Lys Val Gly Ile Asn Pro Lys Ile Asn Asn Leu
            115                 120                 125
Met Pro Gly Tyr Glu Val Ala Lys Tyr Asp Leu Ile Trp Ile Cys Asp
    130                 135                 140
Ser Gly Ile Arg Val Ile Pro Asp Thr Leu Thr Asp Met Val Asn Gln
145                 150                 155                 160
Met Thr Glu Lys Val Gly Leu Val His Gly Leu Pro Tyr Val Ala Asp
                165                 170                 175
Arg Gln Gly Phe Ala Ala Thr Leu Glu Gln Val Tyr Phe Gly Thr Ser
            180                 185                 190
His Pro Arg Tyr Tyr Ile Ser Ala Asn Val Thr Gly Phe Lys Cys Val
        195                 200                 205
Thr Gly Met Ser Cys Leu Met Arg Lys Asp Val Leu Asp Gln Ala Gly
    210                 215                 220
Gly Leu Ile Ala Phe Ala Gln Tyr Ile Ala Glu Asp Tyr Phe Met Ala
225                 230                 235                 240
Lys Ala Ile Ala Asp Arg Gly Trp Arg Phe Ala Met Ser Thr Gln Val
                245                 250                 255
Ala Met Gln Asn Ser Gly Ser Tyr Ser Ile Ser Gln Phe Gln Ser Arg
            260                 265                 270
Met Ile Arg Trp Thr Lys Leu Arg Ile Asn Met Leu Pro Ala Thr Ile
        275                 280                 285
Ile Cys Glu Pro Ile Ser Glu Cys Phe Val Ala Ser Leu Ile Ile Gly
    290                 295                 300
Trp Ala Ala His His Val Phe Arg Trp Asp Ile Met Val Phe Phe Met
305                 310                 315                 320
Cys His Cys Leu Ala Trp Phe Ile Phe Asp Tyr Ile Gln Leu Arg Gly
                325                 330                 335
Val Gln Gly Gly Thr Leu Cys Phe Ser Lys Leu Asp Tyr Ala Val Ala
            340                 345                 350
Trp Phe Ile Arg Glu Ser Met Thr Ile Tyr Ile Phe Leu Ser Ala Leu
        355                 360                 365
Trp Asp Pro Thr Ile Ser Trp Arg Thr Gly Arg Tyr Arg Leu Arg Cys
    370                 375                 380
Gly Gly Thr Ala Glu Glu Ile Leu Asp Val
385                 390

<210> SEQ ID NO 4
<211> LENGTH: 2527
<212> TYPE: PRT
<213> ORGANISM: Homo sapiens
<220> FEATURE:
<221> NAME/KEY: misc_feature
<223> OTHER INFORMATION: Leucine-rich repeat serine/threonine-protein
      kinase 2

<400> SEQUENCE: 4

Met Ala Ser Gly Ser Cys Gln Gly Cys Glu Glu Asp Glu Glu Thr Leu
1               5                   10                  15
Lys Lys Leu Ile Val Arg Leu Asn Asn Val Gln Glu Gly Lys Gln Ile
            20                  25                  30
Glu Thr Leu Val Gln Ile Leu Glu Asp Leu Leu Val Phe Thr Tyr Ser
        35                  40                  45
Glu His Ala Ser Lys Leu Phe Gln Gly Lys Asn Ile His Val Pro Leu
    50                  55                  60
Leu Ile Val Leu Asp Ser Tyr Met Arg Val Ala Ser Val Gln Gln Val
```

-continued

```
                65                  70                  75                  80
Gly Trp Ser Leu Leu Cys Lys Leu Ile Glu Val Cys Pro Gly Thr Met
                    85                  90                  95
Gln Ser Leu Met Gly Pro Gln Asp Val Gly Asn Asp Trp Glu Val Leu
                    100                 105                 110
Gly Val His Gln Leu Ile Leu Lys Met Leu Thr Val His Asn Ala Ser
                    115                 120                 125
Val Asn Leu Ser Val Ile Gly Leu Lys Thr Leu Asp Leu Leu Leu Thr
                    130                 135                 140
Ser Gly Lys Ile Thr Leu Leu Ile Leu Asp Glu Ser Asp Ile Phe
145                 150                 155                 160
Met Leu Ile Phe Asp Ala Met His Ser Phe Pro Ala Asn Asp Glu Val
                    165                 170                 175
Gln Lys Leu Gly Cys Lys Ala Leu His Val Leu Phe Glu Arg Val Ser
                    180                 185                 190
Glu Glu Gln Leu Thr Glu Phe Val Glu Asn Lys Asp Tyr Met Ile Leu
                    195                 200                 205
Leu Ser Ala Leu Thr Asn Phe Lys Asp Glu Glu Ile Val Leu His
    210                 215                 220
Val Leu His Cys Leu His Ser Leu Ala Ile Pro Cys Asn Asn Val Glu
225                 230                 235                 240
Val Leu Met Ser Gly Asn Val Arg Cys Tyr Asn Ile Val Val Glu Ala
                    245                 250                 255
Met Lys Ala Phe Pro Met Ser Glu Arg Ile Gln Glu Val Ser Cys Cys
                    260                 265                 270
Leu Leu His Arg Leu Thr Leu Gly Asn Phe Phe Asn Ile Leu Val Leu
                    275                 280                 285
Asn Glu Val His Glu Phe Val Val Lys Ala Val Gln Gln Tyr Pro Glu
                    290                 295                 300
Asn Ala Ala Leu Gln Ile Ser Ala Leu Ser Cys Leu Ala Leu Leu Thr
305                 310                 315                 320
Glu Thr Ile Phe Leu Asn Gln Asp Leu Glu Glu Lys Asn Glu Asn Gln
                    325                 330                 335
Glu Asn Asp Asp Glu Gly Glu Glu Asp Lys Leu Phe Trp Leu Glu Ala
                    340                 345                 350
Cys Tyr Lys Ala Leu Thr Trp His Arg Lys Asn Lys His Val Gln Glu
                    355                 360                 365
Ala Ala Cys Trp Ala Leu Asn Asn Leu Leu Met Tyr Gln Asn Ser Leu
    370                 375                 380
His Glu Lys Ile Gly Asp Glu Asp Gly His Phe Pro Ala His Arg Glu
385                 390                 395                 400
Val Met Leu Ser Met Leu Met His Ser Ser Lys Glu Val Phe Gln
                    405                 410                 415
Ala Ser Ala Asn Ala Leu Ser Thr Leu Leu Glu Gln Asn Val Asn Phe
                    420                 425                 430
Arg Lys Ile Leu Leu Ser Lys Gly Ile His Leu Asn Val Leu Glu Leu
                    435                 440                 445
Met Gln Lys His Ile His Ser Pro Glu Val Ala Glu Ser Gly Cys Lys
                    450                 455                 460
Met Leu Asn His Leu Phe Glu Gly Ser Asn Thr Ser Leu Asp Ile Met
465                 470                 475                 480
Ala Ala Val Val Pro Lys Ile Leu Thr Val Met Lys Arg His Glu Thr
                    485                 490                 495
```

```
Ser Leu Pro Val Gln Leu Glu Ala Leu Arg Ala Ile Leu His Phe Ile
            500                 505                 510

Val Pro Gly Met Pro Glu Glu Ser Arg Glu Asp Thr Glu Phe His His
            515                 520                 525

Lys Leu Asn Met Val Lys Lys Gln Cys Phe Lys Asn Asp Ile His Lys
        530                 535                 540

Leu Val Leu Ala Ala Leu Asn Arg Phe Ile Gly Asn Pro Gly Ile Gln
545                 550                 555                 560

Lys Cys Gly Leu Lys Val Ile Ser Ser Ile Val His Phe Pro Asp Ala
                565                 570                 575

Leu Glu Met Leu Ser Leu Glu Gly Ala Met Asp Ser Val Leu His Thr
            580                 585                 590

Leu Gln Met Tyr Pro Asp Asp Gln Glu Ile Gln Cys Leu Gly Leu Ser
        595                 600                 605

Leu Ile Gly Tyr Leu Ile Thr Lys Lys Asn Val Phe Ile Gly Thr Gly
    610                 615                 620

His Leu Leu Ala Lys Ile Leu Val Ser Ser Leu Tyr Arg Phe Lys Asp
625                 630                 635                 640

Val Ala Glu Ile Gln Thr Lys Gly Phe Gln Thr Ile Leu Ala Ile Leu
                645                 650                 655

Lys Leu Ser Ala Ser Phe Ser Lys Leu Leu Val His His Ser Phe Asp
            660                 665                 670

Leu Val Ile Phe His Gln Met Ser Ser Asn Ile Met Glu Gln Lys Asp
        675                 680                 685

Gln Gln Phe Leu Asn Leu Cys Cys Lys Cys Phe Ala Lys Val Ala Met
    690                 695                 700

Asp Asp Tyr Leu Lys Asn Val Met Leu Glu Arg Ala Cys Asp Gln Asn
705                 710                 715                 720

Asn Ser Ile Met Val Glu Cys Leu Leu Leu Gly Ala Asp Ala Asn
                725                 730                 735

Gln Ala Lys Glu Gly Ser Ser Leu Ile Cys Gln Val Cys Glu Lys Glu
            740                 745                 750

Ser Ser Pro Lys Leu Val Glu Leu Leu Asn Ser Gly Ser Arg Glu
        755                 760                 765

Gln Asp Val Arg Lys Ala Leu Thr Ile Ser Ile Gly Lys Gly Asp Ser
    770                 775                 780

Gln Ile Ile Ser Leu Leu Leu Arg Arg Leu Ala Leu Asp Val Ala Asn
785                 790                 795                 800

Asn Ser Ile Cys Leu Gly Gly Phe Cys Ile Gly Lys Val Glu Pro Ser
                805                 810                 815

Trp Leu Gly Pro Leu Phe Pro Asp Lys Thr Ser Asn Leu Arg Lys Gln
            820                 825                 830

Thr Asn Ile Ala Ser Thr Leu Ala Arg Met Val Ile Arg Tyr Gln Met
        835                 840                 845

Lys Ser Ala Val Glu Glu Gly Thr Ala Ser Gly Ser Asp Gly Asn Phe
    850                 855                 860

Ser Glu Asp Val Leu Ser Lys Phe Asp Glu Trp Thr Phe Ile Pro Asp
865                 870                 875                 880

Ser Ser Met Asp Ser Val Phe Ala Gln Ser Asp Leu Asp Ser Glu
                885                 890                 895

Gly Ser Glu Gly Ser Phe Leu Val Lys Lys Ser Asn Ser Ile Ser
            900                 905                 910
```

-continued

Val Gly Glu Phe Tyr Arg Asp Ala Val Leu Gln Arg Cys Ser Pro Asn
            915                 920                 925

Leu Gln Arg His Ser Asn Ser Leu Gly Pro Ile Phe Asp His Glu Asp
930                 935                 940

Leu Leu Lys Arg Lys Arg Lys Ile Leu Ser Ser Asp Ser Leu Arg
945                 950                 955                 960

Ser Ser Lys Leu Gln Ser His Met Arg His Ser Asp Ser Ile Ser Ser
            965                 970                 975

Leu Ala Ser Glu Arg Glu Tyr Ile Thr Ser Leu Asp Leu Ser Ala Asn
                980                 985                 990

Glu Leu Arg Asp Ile Asp Ala Leu Ser Gln Lys Cys Cys Ile Ser Val
            995                 1000                1005

His Leu Glu His Leu Glu Lys Leu Glu Leu His Gln Asn Ala Leu
    1010                1015                1020

Thr Ser Phe Pro Gln Gln Leu Cys Glu Thr Leu Lys Ser Leu Thr
    1025                1030                1035

His Leu Asp Leu His Ser Asn Lys Phe Thr Ser Phe Pro Ser Tyr
    1040                1045                1050

Leu Leu Lys Met Ser Cys Ile Ala Asn Leu Asp Val Ser Arg Asn
    1055                1060                1065

Asp Ile Gly Pro Ser Val Val Leu Asp Pro Thr Val Lys Cys Pro
    1070                1075                1080

Thr Leu Lys Gln Phe Asn Leu Ser Tyr Asn Gln Leu Ser Phe Val
    1085                1090                1095

Pro Glu Asn Leu Thr Asp Val Val Glu Lys Leu Glu Gln Leu Ile
    1100                1105                1110

Leu Glu Gly Asn Lys Ile Ser Gly Ile Cys Ser Pro Leu Arg Leu
    1115                1120                1125

Lys Glu Leu Lys Ile Leu Asn Leu Ser Lys Asn His Ile Ser Ser
    1130                1135                1140

Leu Ser Glu Asn Phe Leu Glu Ala Cys Pro Lys Val Glu Ser Phe
    1145                1150                1155

Ser Ala Arg Met Asn Phe Leu Ala Ala Met Pro Phe Leu Pro Pro
    1160                1165                1170

Ser Met Thr Ile Leu Lys Leu Ser Gln Asn Lys Phe Ser Cys Ile
    1175                1180                1185

Pro Glu Ala Ile Leu Asn Leu Pro His Leu Arg Ser Leu Asp Met
    1190                1195                1200

Ser Ser Asn Asp Ile Gln Tyr Leu Pro Gly Pro Ala His Trp Lys
    1205                1210                1215

Ser Leu Asn Leu Arg Glu Leu Leu Phe Ser His Asn Gln Ile Ser
    1220                1225                1230

Ile Leu Asp Leu Ser Glu Lys Ala Tyr Leu Trp Ser Arg Val Glu
    1235                1240                1245

Lys Leu His Leu Ser His Asn Lys Leu Lys Glu Ile Pro Pro Glu
    1250                1255                1260

Ile Gly Cys Leu Glu Asn Leu Thr Ser Leu Asp Val Ser Tyr Asn
    1265                1270                1275

Leu Glu Leu Arg Ser Phe Pro Asn Glu Met Gly Lys Leu Ser Lys
    1280                1285                1290

Ile Trp Asp Leu Pro Leu Asp Glu Leu His Leu Asn Phe Asp Phe
    1295                1300                1305

Lys His Ile Gly Cys Lys Ala Lys Asp Ile Ile Arg Phe Leu Gln

-continued

```
            1310                1315                1320

Gln Arg Leu Lys Lys Ala Val Pro Tyr Asn Arg Met Lys Leu Met
        1325                1330                1335

Ile Val Gly Asn Thr Gly Ser Gly Lys Thr Thr Leu Leu Gln Gln
    1340                1345                1350

Leu Met Lys Thr Lys Lys Ser Asp Leu Gly Met Gln Ser Ala Thr
        1355                1360                1365

Val Gly Ile Asp Val Lys Asp Trp Pro Ile Gln Ile Arg Asp Lys
    1370                1375                1380

Arg Lys Arg Asp Leu Val Leu Asn Val Trp Asp Phe Ala Gly Arg
        1385                1390                1395

Glu Glu Phe Tyr Ser Thr His Pro His Phe Met Thr Gln Arg Ala
    1400                1405                1410

Leu Tyr Leu Ala Val Tyr Asp Leu Ser Lys Gly Gln Ala Glu Val
        1415                1420                1425

Asp Ala Met Lys Pro Trp Leu Phe Asn Ile Lys Ala Arg Ala Ser
    1430                1435                1440

Ser Ser Pro Val Ile Leu Val Gly Thr His Leu Asp Val Ser Asp
        1445                1450                1455

Glu Lys Gln Arg Lys Ala Cys Met Ser Lys Ile Thr Lys Glu Leu
    1460                1465                1470

Leu Asn Lys Arg Gly Phe Pro Ala Ile Arg Asp Tyr His Phe Val
        1475                1480                1485

Asn Ala Thr Glu Glu Ser Asp Ala Leu Ala Lys Leu Arg Lys Thr
    1490                1495                1500

Ile Ile Asn Glu Ser Leu Asn Phe Lys Ile Arg Asp Gln Leu Val
    1505                1510                1515

Val Gly Gln Leu Ile Pro Asp Cys Tyr Val Glu Leu Glu Lys Ile
    1520                1525                1530

Ile Leu Ser Glu Arg Lys Asn Val Pro Ile Glu Phe Pro Val Ile
    1535                1540                1545

Asp Arg Lys Arg Leu Leu Gln Leu Val Arg Glu Asn Gln Leu Gln
    1550                1555                1560

Leu Asp Glu Asn Glu Leu Pro His Ala Val His Phe Leu Asn Glu
    1565                1570                1575

Ser Gly Val Leu Leu His Phe Gln Asp Pro Ala Leu Gln Leu Ser
    1580                1585                1590

Asp Leu Tyr Phe Val Glu Pro Lys Trp Leu Cys Lys Ile Met Ala
    1595                1600                1605

Gln Ile Leu Thr Val Lys Val Glu Gly Cys Pro Lys His Pro Lys
    1610                1615                1620

Gly Ile Ile Ser Arg Arg Asp Val Glu Lys Phe Leu Ser Lys Lys
    1625                1630                1635

Arg Lys Phe Pro Lys Asn Tyr Met Ser Gln Tyr Phe Lys Leu Leu
    1640                1645                1650

Glu Lys Phe Gln Ile Ala Leu Pro Ile Gly Glu Glu Tyr Leu Leu
    1655                1660                1665

Val Pro Ser Ser Leu Ser Asp His Arg Pro Val Ile Glu Leu Pro
    1670                1675                1680

His Cys Glu Asn Ser Glu Ile Ile Ile Arg Leu Tyr Glu Met Pro
    1685                1690                1695

Tyr Phe Pro Met Gly Phe Trp Ser Arg Leu Ile Asn Arg Leu Leu
    1700                1705                1710
```

```
Glu Ile Ser Pro Tyr Met Leu Ser Gly Arg Glu Arg Ala Leu Arg
1715                1720                1725

Pro Asn Arg Met Tyr Trp Arg Gln Gly Ile Tyr Leu Asn Trp Ser
1730                1735                1740

Pro Glu Ala Tyr Cys Leu Val Gly Ser Glu Val Leu Asp Asn His
1745                1750                1755

Pro Glu Ser Phe Leu Lys Ile Thr Val Pro Ser Cys Arg Lys Gly
1760                1765                1770

Cys Ile Leu Leu Gly Gln Val Val Asp His Ile Asp Ser Leu Met
1775                1780                1785

Glu Glu Trp Phe Pro Gly Leu Leu Glu Ile Asp Ile Cys Gly Glu
1790                1795                1800

Gly Glu Thr Leu Leu Lys Lys Trp Ala Leu Tyr Ser Phe Asn Asp
1805                1810                1815

Gly Glu Glu His Gln Lys Ile Leu Leu Asp Asp Leu Met Lys Lys
1820                1825                1830

Ala Glu Glu Gly Asp Leu Leu Val Asn Pro Asp Gln Pro Arg Leu
1835                1840                1845

Thr Ile Pro Ile Ser Gln Ile Ala Pro Asp Leu Ile Leu Ala Asp
1850                1855                1860

Leu Pro Arg Asn Ile Met Leu Asn Asn Asp Glu Leu Glu Phe Glu
1865                1870                1875

Gln Ala Pro Glu Phe Leu Leu Gly Asp Gly Ser Phe Gly Ser Val
1880                1885                1890

Tyr Arg Ala Ala Tyr Glu Gly Glu Glu Val Ala Val Lys Ile Phe
1895                1900                1905

Asn Lys His Thr Ser Leu Arg Leu Leu Arg Gln Glu Leu Val Val
1910                1915                1920

Leu Cys His Leu His His Pro Ser Leu Ile Ser Leu Leu Ala Ala
1925                1930                1935

Gly Ile Arg Pro Arg Met Leu Val Met Glu Leu Ala Ser Lys Gly
1940                1945                1950

Ser Leu Asp Arg Leu Leu Gln Gln Asp Lys Ala Ser Leu Thr Arg
1955                1960                1965

Thr Leu Gln His Arg Ile Ala Leu His Val Ala Asp Gly Leu Arg
1970                1975                1980

Tyr Leu His Ser Ala Met Ile Ile Tyr Arg Asp Leu Lys Pro His
1985                1990                1995

Asn Val Leu Leu Phe Thr Leu Tyr Pro Asn Ala Ala Ile Ile Ala
2000                2005                2010

Lys Ile Ala Asp Tyr Gly Ile Ala Gln Tyr Cys Cys Arg Met Gly
2015                2020                2025

Ile Lys Thr Ser Glu Gly Thr Pro Gly Phe Arg Ala Pro Glu Val
2030                2035                2040

Ala Arg Gly Asn Val Ile Tyr Asn Gln Gln Ala Asp Val Tyr Ser
2045                2050                2055

Phe Gly Leu Leu Leu Tyr Asp Ile Leu Thr Thr Gly Gly Arg Ile
2060                2065                2070

Val Glu Gly Leu Lys Phe Pro Asn Glu Phe Asp Glu Leu Glu Ile
2075                2080                2085

Gln Gly Lys Leu Pro Asp Pro Val Lys Glu Tyr Gly Cys Ala Pro
2090                2095                2100
```

-continued

Trp Pro Met Val Glu Lys Leu Ile Lys Gln Cys Leu Lys Glu Asn
    2105            2110             2115

Pro Gln Glu Arg Pro Thr Ser Ala Gln Val Phe Asp Ile Leu Asn
    2120            2125             2130

Ser Ala Glu Leu Val Cys Leu Thr Arg Arg Ile Leu Leu Pro Lys
    2135            2140             2145

Asn Val Ile Val Glu Cys Met Val Ala Thr His His Asn Ser Arg
    2150            2155             2160

Asn Ala Ser Ile Trp Leu Gly Cys Gly His Thr Asp Arg Gly Gln
    2165            2170             2175

Leu Ser Phe Leu Asp Leu Asn Thr Glu Gly Tyr Thr Ser Glu Glu
    2180            2185             2190

Val Ala Asp Ser Arg Ile Leu Cys Leu Ala Leu Val His Leu Pro
    2195            2200             2205

Val Glu Lys Glu Ser Trp Ile Val Ser Gly Thr Gln Ser Gly Thr
    2210            2215             2220

Leu Leu Val Ile Asn Thr Glu Asp Gly Lys Lys Arg His Thr Leu
    2225            2230             2235

Glu Lys Met Thr Asp Ser Val Thr Cys Leu Tyr Cys Asn Ser Phe
    2240            2245             2250

Ser Lys Gln Ser Lys Gln Lys Asn Phe Leu Leu Val Gly Thr Ala
    2255            2260             2265

Asp Gly Lys Leu Ala Ile Phe Glu Asp Lys Thr Val Lys Leu Lys
    2270            2275             2280

Gly Ala Ala Pro Leu Lys Ile Leu Asn Ile Gly Asn Val Ser Thr
    2285            2290             2295

Pro Leu Met Cys Leu Ser Glu Ser Thr Asn Ser Thr Glu Arg Asn
    2300            2305             2310

Val Met Trp Gly Gly Cys Gly Thr Lys Ile Phe Ser Phe Ser Asn
    2315            2320             2325

Asp Phe Thr Ile Gln Lys Leu Ile Glu Thr Arg Thr Ser Gln Leu
    2330            2335             2340

Phe Ser Tyr Ala Ala Phe Ser Asp Ser Asn Ile Ile Thr Val Val
    2345            2350             2355

Val Asp Thr Ala Leu Tyr Ile Ala Lys Gln Asn Ser Pro Val Val
    2360            2365             2370

Glu Val Trp Asp Lys Lys Thr Glu Lys Leu Cys Gly Leu Ile Asp
    2375            2380             2385

Cys Val His Phe Leu Arg Glu Val Met Val Lys Glu Asn Lys Glu
    2390            2395             2400

Ser Lys His Lys Met Ser Tyr Ser Gly Arg Val Lys Thr Leu Cys
    2405            2410             2415

Leu Gln Lys Asn Thr Ala Leu Trp Ile Gly Thr Gly Gly Gly His
    2420            2425             2430

Ile Leu Leu Leu Asp Leu Ser Thr Arg Arg Leu Ile Arg Val Ile
    2435            2440             2445

Tyr Asn Phe Cys Asn Ser Val Arg Val Met Met Thr Ala Gln Leu
    2450            2455             2460

Gly Ser Leu Lys Asn Val Met Leu Val Leu Gly Tyr Asn Arg Lys
    2465            2470             2475

Asn Thr Glu Gly Thr Gln Lys Gln Lys Glu Ile Gln Ser Cys Leu
    2480            2485             2490

Thr Val Trp Asp Ile Asn Leu Pro His Glu Val Gln Asn Leu Glu

```
                    2495                2500                2505
Lys His  Ile Glu Val Arg Lys  Glu Leu Ala Glu Lys  Met Arg Arg
        2510                2515                2520

Thr Ser  Val Glu
        2525

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
ccggatggct ggagctatt                                                       19

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
tgttcaggct ggagactat                                                       19

<210> SEQ ID NO 7
<211> LENGTH: 21
<212> TYPE: RNA
<213> ORGANISM: Artificial Sequence
<220> FEATURE:
<223> OTHER INFORMATION: Synthetic

<400> SEQUENCE: 7
aaauguucag gcuggagacu a                                                    21
```